US011338093B2

(12) United States Patent
Hewson et al.

(10) Patent No.: US 11,338,093 B2
(45) Date of Patent: May 24, 2022

(54) DOSE SETTING MECHANISM

(71) Applicant: NORTON HEALTHCARE LIMITED, West Yorkshire (GB)

(72) Inventors: Karl James Hewson, Cambridgeshire (GB); Jeremy James Robert Kooyman, Cambridgeshire (GB); Xorge Castro Pelayo, Cambridgeshire (GB)

(73) Assignee: Norton Healthcare Limited, West Yorkshire (GB)

( * ) Notice: Subject to any disclaimer, the term of this patent is extended or adjusted under 35 U.S.C. 154(b) by 131 days.

(21) Appl. No.: 16/332,032

(22) PCT Filed: Sep. 11, 2017

(86) PCT No.: PCT/EP2017/072714
§ 371 (c)(1),
(2) Date: Mar. 11, 2019

(87) PCT Pub. No.: WO2018/046717
PCT Pub. Date: Mar. 15, 2018

(65) Prior Publication Data
US 2019/0366009 A1    Dec. 5, 2019

(30) Foreign Application Priority Data
Sep. 12, 2016 (GB) .................... 1615442

(51) Int. Cl.
*A61M 5/315* (2006.01)
*A61M 5/20* (2006.01)
*A61M 5/31* (2006.01)

(52) U.S. Cl.
CPC ...... *A61M 5/31553* (2013.01); *A61M 5/2033* (2013.01); *A61M 5/31541* (2013.01);
(Continued)

(58) Field of Classification Search
CPC .......... A61M 5/31541; A61M 5/31553; A61M 5/31593; A61M 5/31583; A61M 5/2033;
(Continued)

(56) References Cited

U.S. PATENT DOCUMENTS

| 8,920,383 B2 | 12/2014 | Enggaard et al. |
| 2008/0147005 A1 | 6/2008 | Moller et al. |

(Continued)

FOREIGN PATENT DOCUMENTS

| WO | 2006/045528 A1 | 5/2006 |
| WO | 2011/025448 A1 | 3/2011 |

(Continued)

*Primary Examiner* — Amber R Stiles
*Assistant Examiner* — Avery Smale
(74) *Attorney, Agent, or Firm* — BakerHostetler

(57) ABSTRACT

An injection device comprises a housing having a longitudinal axis, an axially-depressible dose button (430), a dose indicator (418), a dose setting mechanism operatively coupled to said dose indicator and capable of setting a dose to be ejected from the injection device and spring capable of storing energy necessary for ejecting the dose from the injection device. The spring (420) is coupled to the dose setting mechanism such that a charging force can be transferred from the dose setting mechanism to the spring to increase the energy stored by the spring. The dose setting mechanism comprises an assembly of three components, including: •a ratchet ring (410) rotationally and axially locked with respect to said housing, the ratchet ring including a ratchet component; •a drive plate (405) including a first set of splines forming a ratchet arrangement with said ratchet component; and•a dose selector (416) capable of being rotated about said longitudinal axis with respect to said housing to set the dose and including splines for disengaging said ratchet arrangement. The ratchet compo-
(Continued)

nent is capable of interacting with both the splines on the dose selector and the splines on the drive plate.

20 Claims, 34 Drawing Sheets

(52) U.S. Cl.
CPC . *A61M 5/31593* (2013.01); *A61M 2005/3126* (2013.01); *A61M 2205/582* (2013.01)

(58) Field of Classification Search
CPC ............ A61M 2005/3126; A61M 5/20; A61M 2005/3125; A61M 5/31525; A61M 5/31526; A61M 5/31528; A61M 5/31533; A61M 5/31545; A61M 5/31548; A61M 5/3155

See application file for complete search history.

(56) References Cited

U.S. PATENT DOCUMENTS

| 2011/0077595 | A1 | | 3/2011 | Eich et al. | |
|---|---|---|---|---|---|
| 2015/0148750 | A1 | * | 5/2015 | Pedersen | ................ A61M 5/20 |
| | | | | | 604/207 |

FOREIGN PATENT DOCUMENTS

| WO | 2013/178372 | A1 | | 12/2013 | |
|---|---|---|---|---|---|
| WO | 2014/161954 | A1 | | 10/2014 | |
| WO | 2015/007820 | A1 | | 1/2015 | |
| WO | WO-2015007820 | A1 | * | 1/2015 | ........ A61M 5/31553 |
| WO | 2015/032780 | A1 | | 3/2015 | |

* cited by examiner

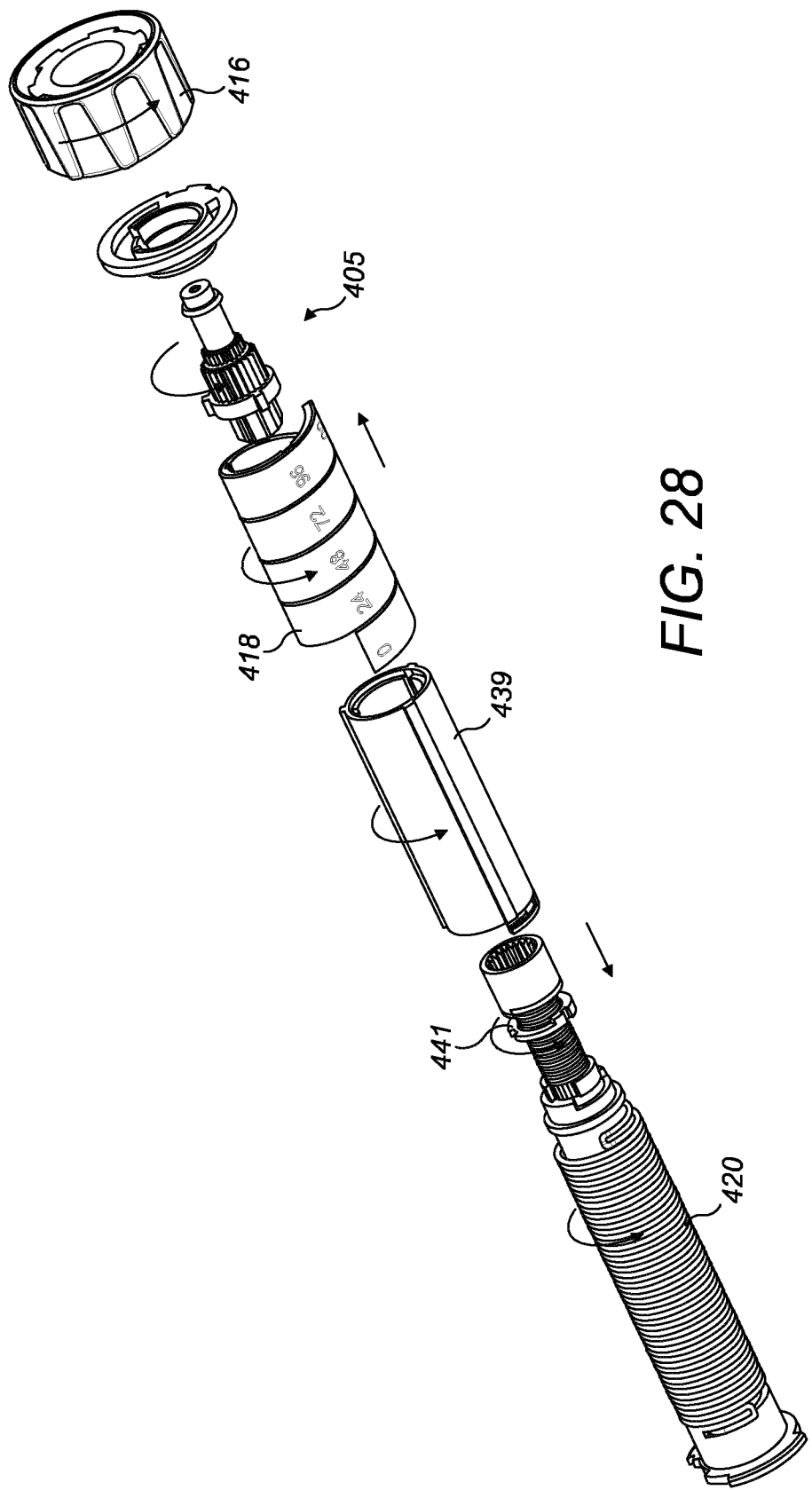

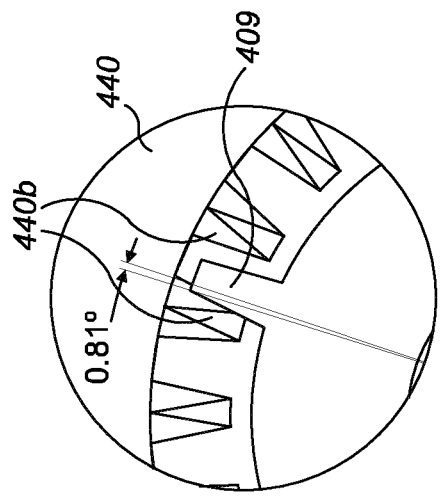
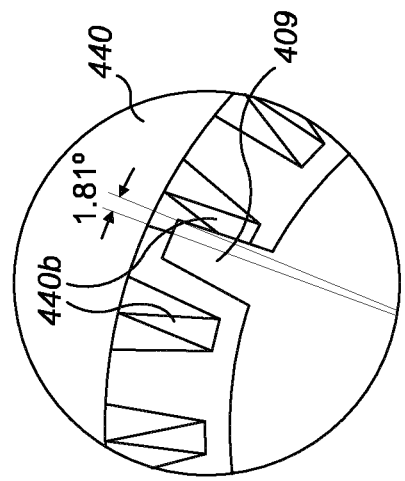
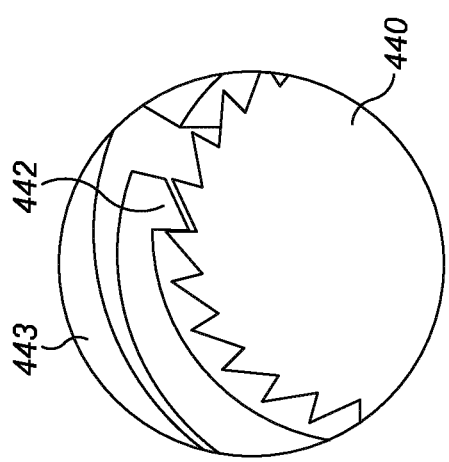
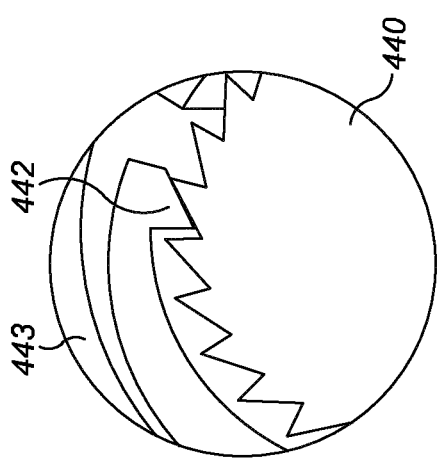
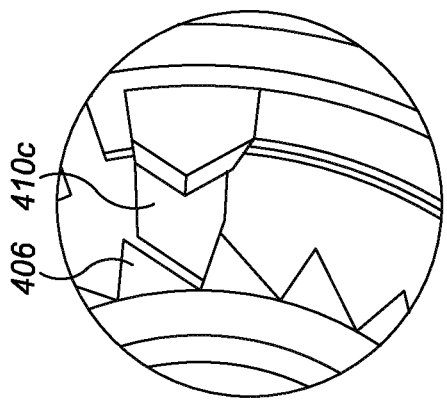
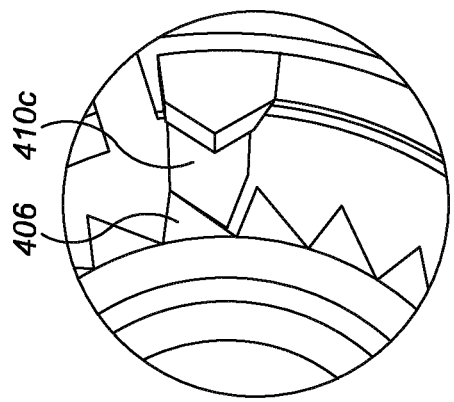
FIG. 40
FIG. 41

DOSE SETTING MECHANISM

CROSS-REFERENCE TO RELATED APPLICATIONS

This application is the National Stage of International Patent Application No. PCT/EP2017/072714, filed Sep. 11, 2017, which claims priority from Great Britain Patent Application No. 1615442.9 filed Sep. 12, 2016, the entire contents of both of which applications are incorporated herein by reference.

This disclosure relates to the field of a dose setting mechanism for an injection device, preferably a reusable pen-type injection device.

BACKGROUND

Certain injection devices have a dose setting member, or dose selector, via which the user can select a desired dose of medicament to be delivered from the injection device. The dose selector can commonly be actuated in one direction to increase the set dose ("dialling up") and actuated in another direction to decrease the set dose ("dialling down"). As the dose is dialled up or down, this correspondingly increases or decreases stored energy in the device (e.g. in a torsion spring). An example of this type of dose setting can be seen in WO2006/045528.

In WO2006/045528, a drive member is connected to a dose setting member via a self-tightening ratchet having saw-toothed teeth. The ratchet enables the dose setting member to be rotated in both directions so that a given dose may be set, whilst preventing the spring from unwinding from the currently selected dose.

Another example of an injection device having this type of ratchet is described in WO2015/032780. A ratchet interface 119 between a dose selector ("dial member 106") and a drive member 108 prevents the spring unwinding.

Such dose setting ratchets have the additional advantage of creating audible and tactile feedback for each dose unit dialled by the user.

In both of the above prior art examples, if the user continues to increase the selected dose until the maximum dose limit is reached, a component abuts a hard endstop on an inner surface of the injection device housing, thus preventing further dialling up of the dose. A disadvantage of this arrangement is that, should the user continue to attempt to increase the dose, damage to components of the injection device may occur.

This issue is mitigated in U.S. Pat. No. 8,920,383 which describes a toothed limiter 10 which has a stopping position in which the dose cannot be further increased. If the user continues to apply torque to the dose setting member, two torque paths are provided such that it is possible to provide a larger torque without breaking parts of the device. In this way, the risk of the user causing damage to the device is reduced.

BRIEF SUMMARY OF THE DISCLOSURE

In accordance with an aspect of the present invention there is provided an injection device comprising:
  a. a housing having a longitudinal axis;
  b. an axially-depressible dose button;
  c. a dose indicator;
  d. a dose setting mechanism operatively coupled to said dose indicator and capable of setting a dose to be ejected from the injection device; and
  e. a spring capable of storing energy necessary for ejecting the dose from the injection device, wherein the spring is coupled to the dose setting mechanism such that a charging force can be transferred from the dose setting mechanism to the spring to increase the energy stored by the spring;
  wherein the dose setting mechanism comprises an assembly of three components, including:
    a ratchet ring rotationally and axially locked with respect to said housing, the ratchet ring including a ratchet component;
    a drive plate including a first set of splines forming a ratchet arrangement with said ratchet component; and
    a dose selector capable of being rotated about said longitudinal axis with respect to said housing to set the dose and including splines for disengaging said ratchet arrangement,
    wherein said ratchet component is capable of interacting with both the splines on the dose selector and the splines on the drive plate.

The assembly of three components provides greater reliability during dose selection. The splines for disengaging the ratchet improve the smoothness of operation during decrementing of the dose. Having a single ratchet component serves two functions, interacting with both the dose selector and the drive plate, which makes the dose setting more reliable.

In an embodiment, the dose selector is operatively connectable to the dose indicator via said ratchet arrangement, the ratchet arrangement preventing counter-rotation of the dose indicator during dose setting. Preferably, the ratchet arrangement is disengagable from the dose selector by axial depression of the dose button.

In an embodiment, the injection device further comprises an over-torque feature located between the dose selector and the spring, the over-torque feature being actuatable, when the rotation of the dose selector causes the charging force to exceed a defined limit, to reduce the charging force transferred from the dose selector to the spring. Preferably, the over-torque feature is capable of reducing the charging force transferred from the dose selector to the spring to substantially zero.

The over-torque feature may comprise a ratchet arrangement between said drive plate and said dose selector. In an embodiment, the ratchet arrangement comprises a ratchet pawl on said dose selector and a second set of splines on said drive plate.

Preferably, the spring is a torsion spring and the charging force transferred to the spring is a charging torque.

In an embodiment, the injection device further comprises a drive assembly having a rotational to axial coupling, where the drive assembly is rotationally drivable by the spring and is arranged to provide an axial force for ejecting the dose from the injection device.

In an embodiment, the spring is fixed at one end to said housing and fixed at the other end to a rotatable drive sleeve. The drive plate may further comprise a third set of splines for engaging and turning said drive sleeve. The drive plate may further comprise a fourth set of splines for engaging said drive assembly.

In an embodiment, the dose indicator comprises a number sleeve. The ratchet ring may include a rotary endstop for said number sleeve.

Preferably, said ratchet component comprises a first pawl capable of interacting with the splines on the dose selector and a second pawl capable of interacting with the splines on the drive plate. Said first pawl and second pawl may be provided on a single ratchet arm which is preferably radially-moveable.

In an embodiment, the injection device further comprises a medicament container. Preferably, the medicament container comprises a pre-filled syringe or cartridge. In an embodiment, medicament is contained in the medicament container, wherein the medicament may be selected from the group comprising: antipsychotic substances including risperidone, hormones, antitoxins, substances for the control of pain, immunosuppressives, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity.

BRIEF DESCRIPTION OF THE DRAWINGS

Embodiments of the invention are further described hereinafter, by way of example only, with reference to the accompanying drawings, in which:

FIG. 28 is an exploded view of components involved in decrementing the dose;

FIG. 40 shows typical relative positions of the hold ratchet, drive plate, drive shaft and chassis;

FIG. 41 shows the most extreme possible relative positions of the hold ratchet, drive plate, drive shaft and chassis;

DETAILED DESCRIPTION

Figure 1:
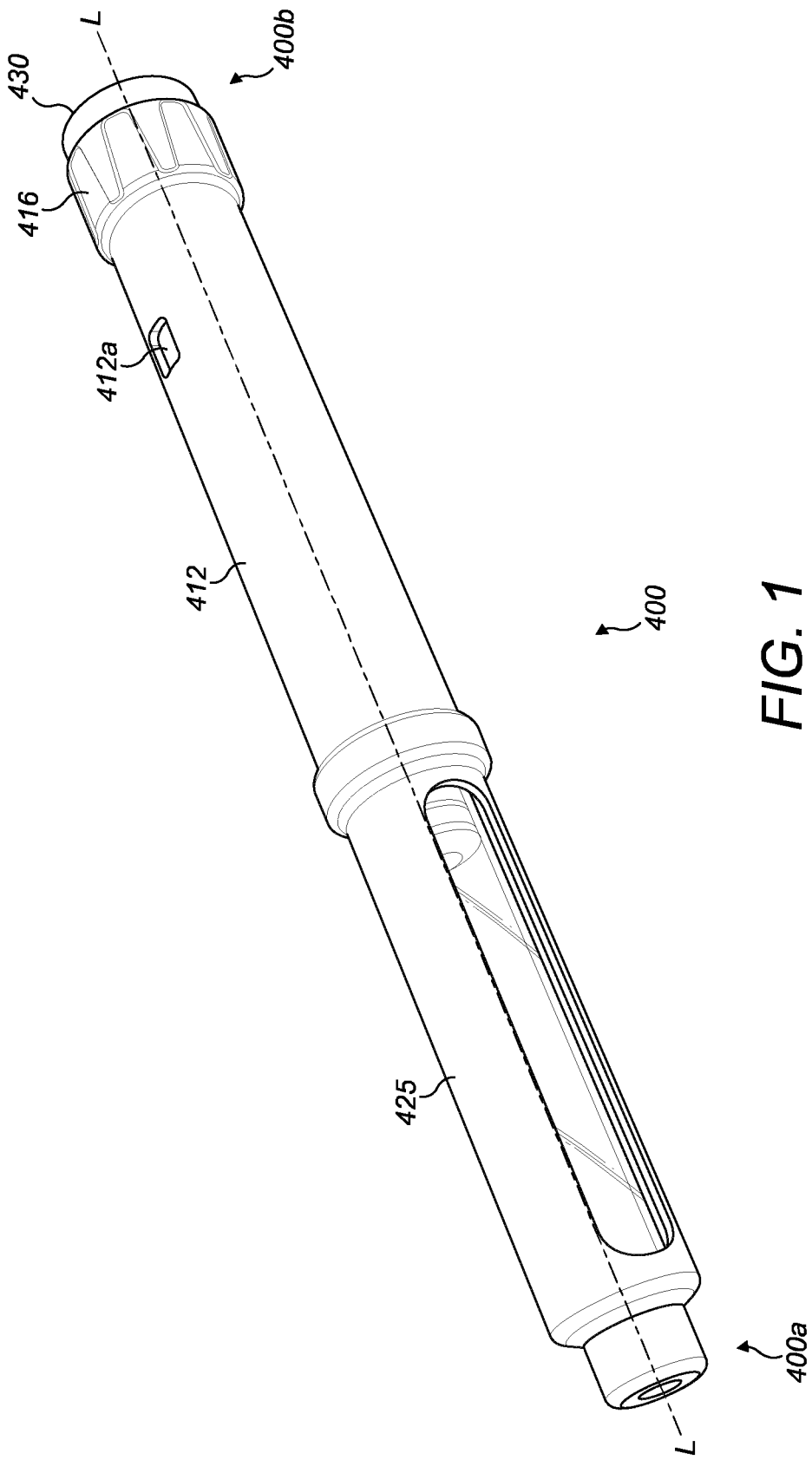
FIG. 1 is a perspective view of an injection device in accordance with an embodiment of the present invention.

In the present disclosure, the following terms may be understood in view of the below explanations:

The term "injection device" may refer to a device intended for the injection of a medicament to the body and includes devices configured for various delivery methods, such as intradermal, subcutaneous, intramuscular, intravenous, intraosseous, intraperitoneal, intrathecal, epidural, intracardiac, intraarticular, intracavernous, and intravitreal, which may include via a cannula, catheter or similar device. Injection device includes syringes of all types, devices that contain said syringes such as auto-injectors, pen-injectors, patch injectors and other similar devices.

The term "pen-injector" may include any device configured to deliver a dose of a medicament from a cartridge.

The term "user" may refer to a medical practitioner, end user or other user associated therewith.

The term "coupling" may refer to a connection between components (not necessarily a direct connection; there may be intermediate components therebetween) that enables a force to be transmitted between the components.

The term "a rotational coupling" may refer to a coupling which enables a rotational force to be transmitted between the components.

The term "operatively connectable" may refer to at least two individual components which are releasably connectable together in such a way that the individual components can work together, for example wherein rotation of one of the individual components effects rotation of all of the operatively connected components.

The term "dose selector" may refer to a component or components which, when actuated by a user, enable a dose of medicament to be selected.

The term "dose indicator" may refer to a component or components which provide a display or indication to the user of the selected dose of medicament.

The term "splines" may refer to one or more ridges, ribs or other protrusions on one component which engage in corresponding grooves or the like on a second component to connect the two components together.

The term "a splined connection" may refer to a connection effected by one or more splines.

The term "forward" or "forwards" may refer to a direction towards the end of the injection device from which medicament is expelled;

The term "backward", "backwards", "rearwards" or "rearwardly" may refer to a direction away from the end of the injection device from which medicament is expelled.

The term "drive assembly" may refer to an assembly of components capable of using a driving force from, for example, a spring, to eject medicament from an injection device.

The term "backlash" may refer to a clearance caused by a gap between mechanical components.

The term "medicament" may include a substance in liquid or gas form. The medicament may be selected from the group comprising of: antipsychotic substances including risperidone, hormones, antitoxins, substances for the control of pain, immunosuppressives, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity.

When referring to the injection device, the term "containing the medicament", may refer to the medicament being contained within a suitable medicament container, such as a pre-filled syringe or cartridge, within the injection device.

The term "ratchet arrangement" may refer to an arrangement of components comprising a set of splines or teeth and a "ratchet component" which can engage in said splines or teeth to permit one-way movement.

The term "over-torque feature" may refer to a feature located on a first component and capable of interacting with a second component so as to reduce a force being transferred along a force path from the first component to the second component, for example by changing the direction of the force path and/or creating an additional force path.

The term "single component" may refer to one component, an integrally-formed component, a unitary component, or at least two component parts fixed together or with respect to one another.

The term "haptic feedback track" may refer to a plurality of ridges, ribs, teeth, or other protrusions on an internal surface of the injection device and with which another component, moving rotationally with respect thereto, can engage to provide audible and/or tactile feedback to a user of the injection device.

The term "a dose button" may refer to a button or the like at the rear of the injection device which is actuated, for example by pressing axially-forwardly with respect to the device housing, in order to initiate dose delivery.

Description of Example Embodiment

Figure 2:
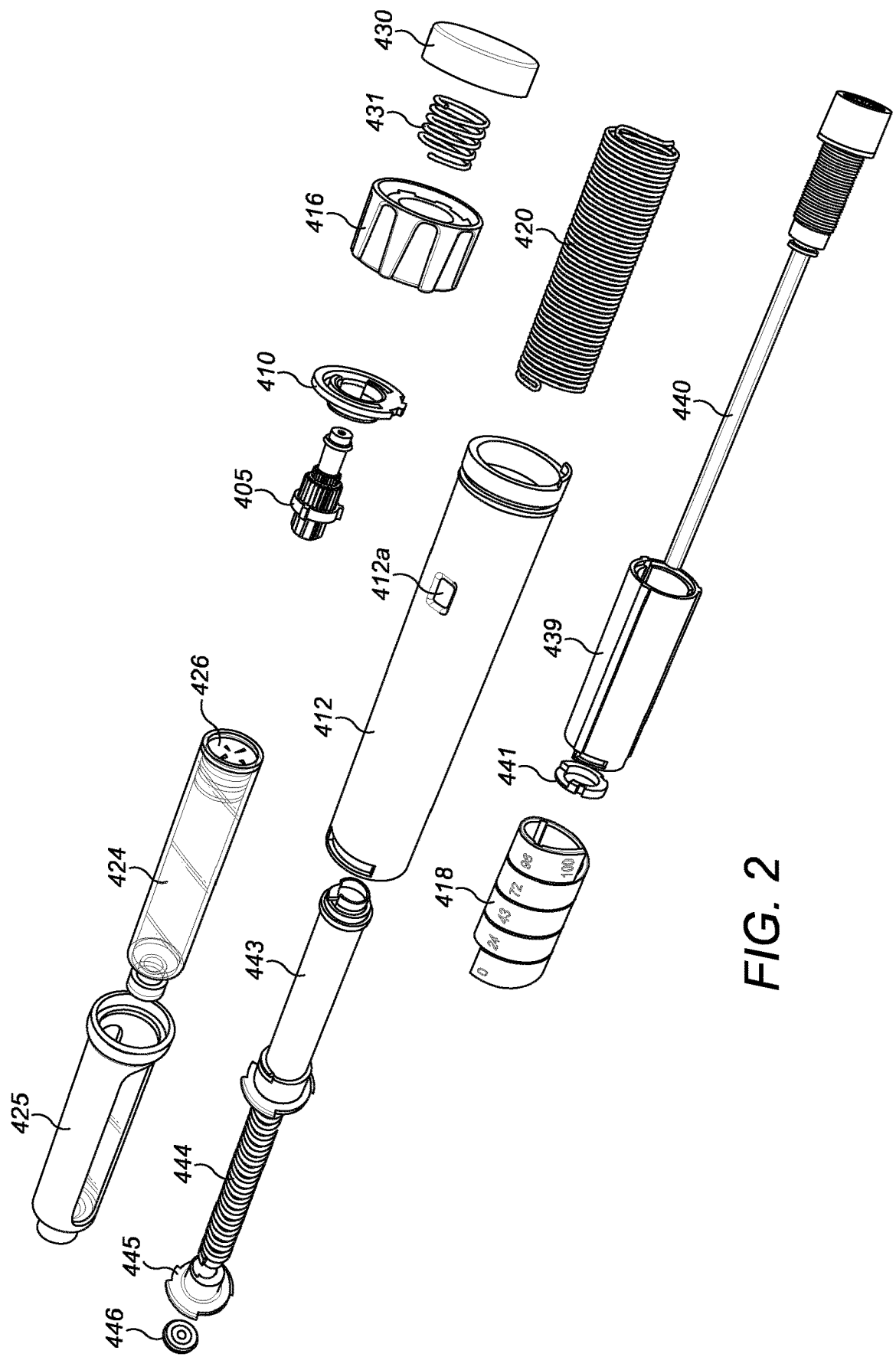
FIG. 2 is an exploded view of the injection device of FIG. 1.
Figure 3:
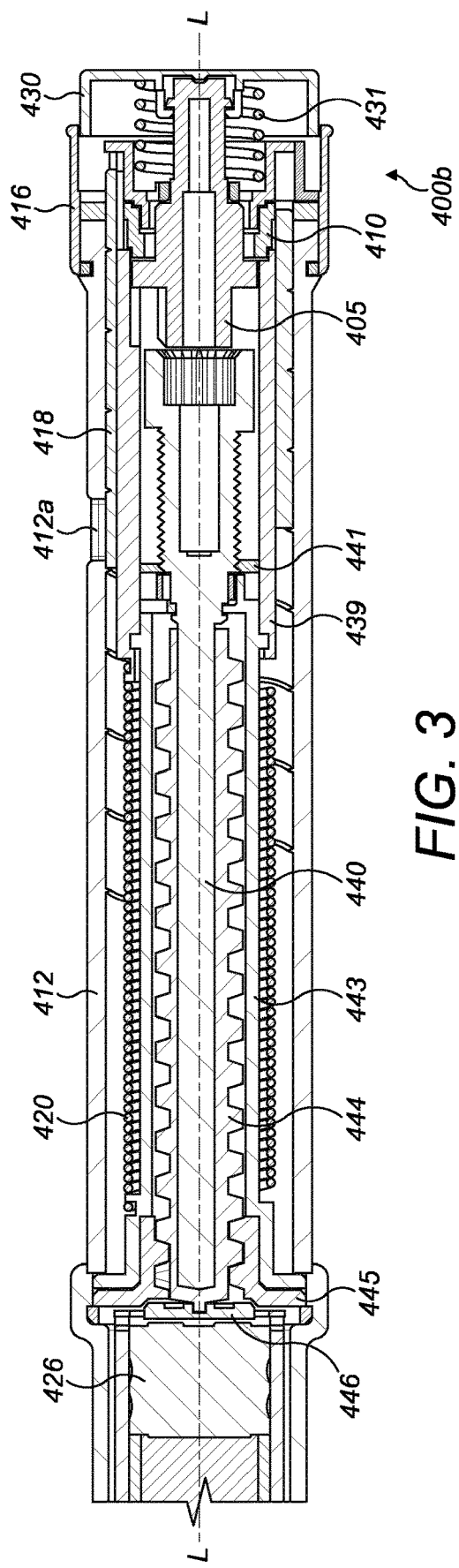
FIG. 3 is a cross-sectional view of selected components of the injection device of FIG. 1.

An injection device 400 according to a non-limiting example embodiment of the present invention is shown in FIGS. 1-3. The injection device 400 is configured to deliver a dose of medicament and extends along a longitudinal axis L between a front end 400a and a rear end 400b of the injection device 400. The injection device 400 has a housing 412 and is able to receive a needle (not shown) at the front end 400a. A dose selector 416 is provided at the rear end 400b and is arranged to permit the selection of a desired dose of medicament for delivery through the needle into an injection site. The housing 412 includes an aperture 412a through which a dose indicator, for example a number sleeve 418 is visible.

A cartridge holder 425 holds a medicament cartridge 424 from which medicament is expelled by the forward axial movement of a cartridge stopper 426. The cartridge stopper 426 is driven axially forward by a drive mechanism described later below.

Referring to FIG. 3, the components of the injection device are arranged generally concentrically about longitudinal axis L. Beginning at the rear end 400b of the injection device 400, a dose button 430 is biased axially rearward by a dose button spring 431. Three interacting components, the dose selector 416, a ratchet ring 410 and a drive plate 405 are involved in a dose setting mechanism which sets the desired dose to be delivered.

A drive spring 420 is attached at one end to a chassis 443 which is fixed with respect to the housing 412. The other end of the drive spring 420 is fixed to a drive sleeve 439.

A last dose nut 441 is threaded to an elongate drive shaft 440. An external surface of the last dose nut 441 has three equally spaced grooves 441a in which internal splines 439b on the drive sleeve engage. The last dose nut 441 also has an endstop 441b for engaging with a correspondingly-shaped endstop 440a on the drive shaft 440.

Figure 31:
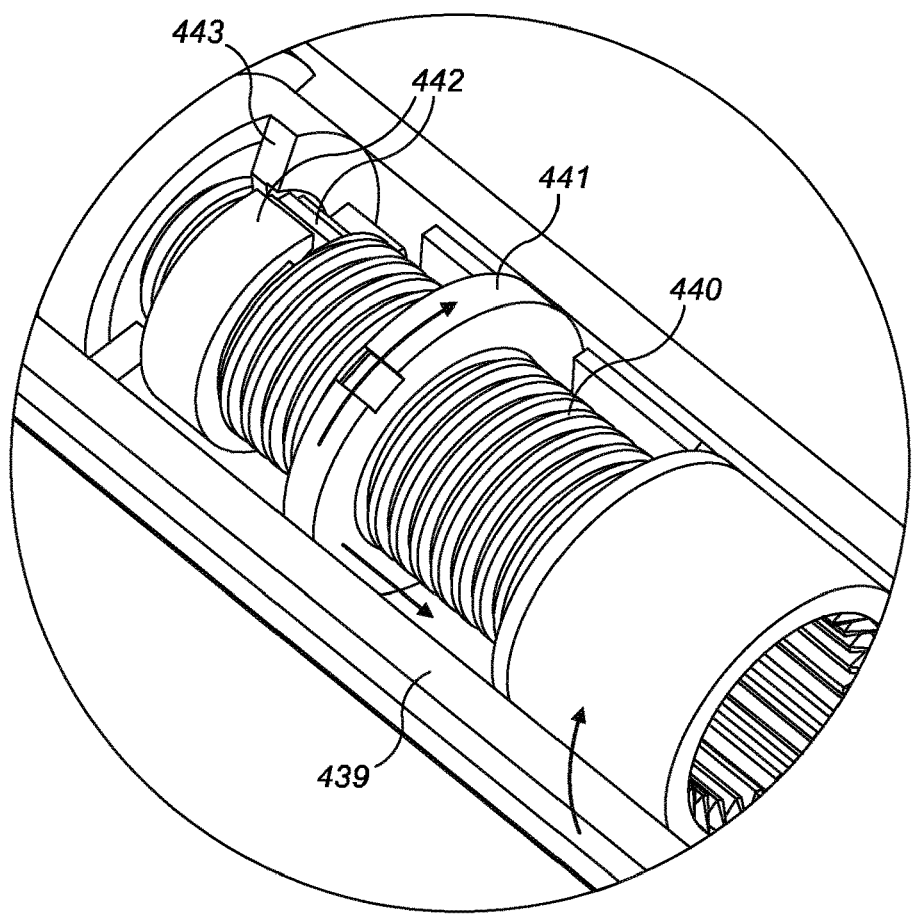
FIGS. 31-33 illustrate the last dose protection feature.
Figure 32:
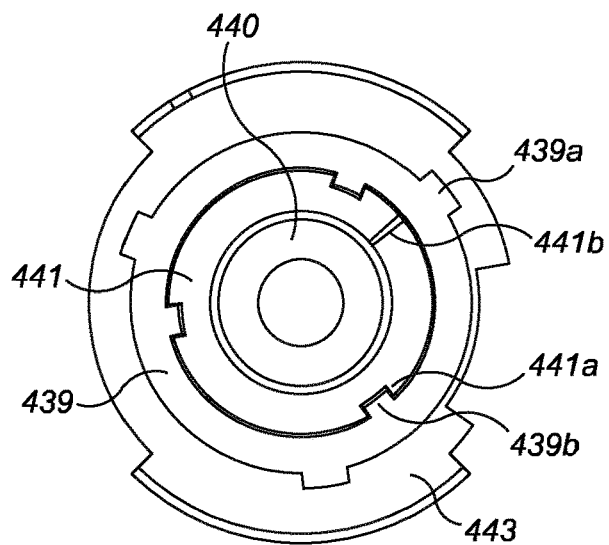
Figure 33:
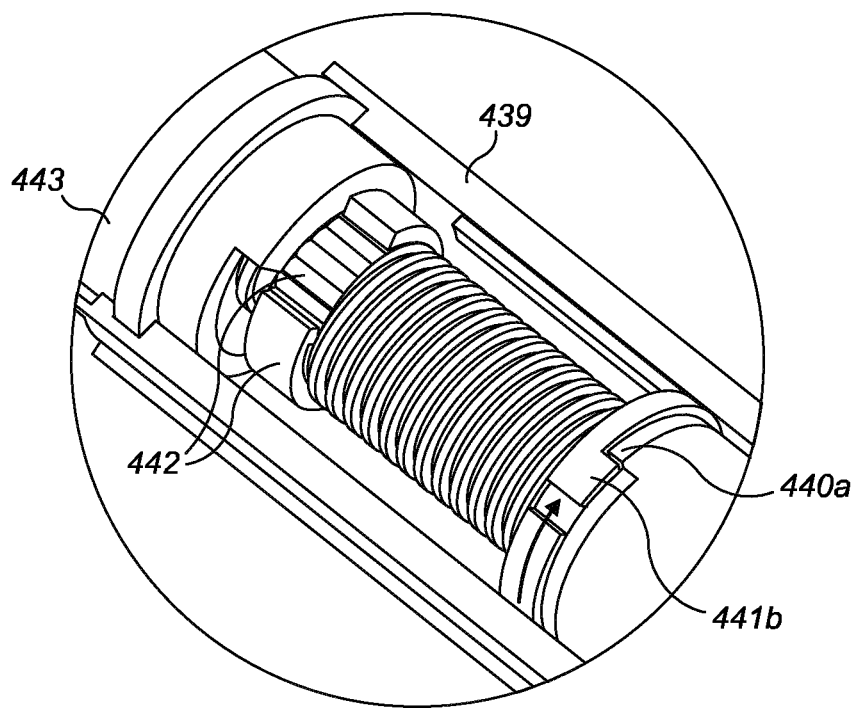

As shown in FIGS. 31-33, the drive shaft 440 is rotationally locked to the chassis 443 by a chassis ratchet 442. The chassis ratchet 442 is a one-way ratchet which locks the drive shaft 440 to the chassis 443 in a clockwise (dose setting) direction, whilst allowing relative rotation of the drive shaft 440 with the chassis 443 in an anti-clockwise (dose delivery) direction. A rear end of the drive shaft 440 is provided with a set of internal splines 440b (FIG. 38B) which can engage with the drive plate 405. A front end of the drive shaft 440 is provided with a set of external splines 440c (FIG. 42) for keying i.e. rotationally locking the drive shaft 440 to a hollow plunger 444.

The hollow plunger 444 is capable of converting rotation of the drive shaft 440 into linear (axial) motion via a thrust nut 445 (an external screw thread of the plunger 444 being engaged with the thrust nut 445). A plunger bearing 446 at the forward end of the plunger 444 can be pushed axially against the cartridge stopper 426 to expel medicament.

Figure 4A:
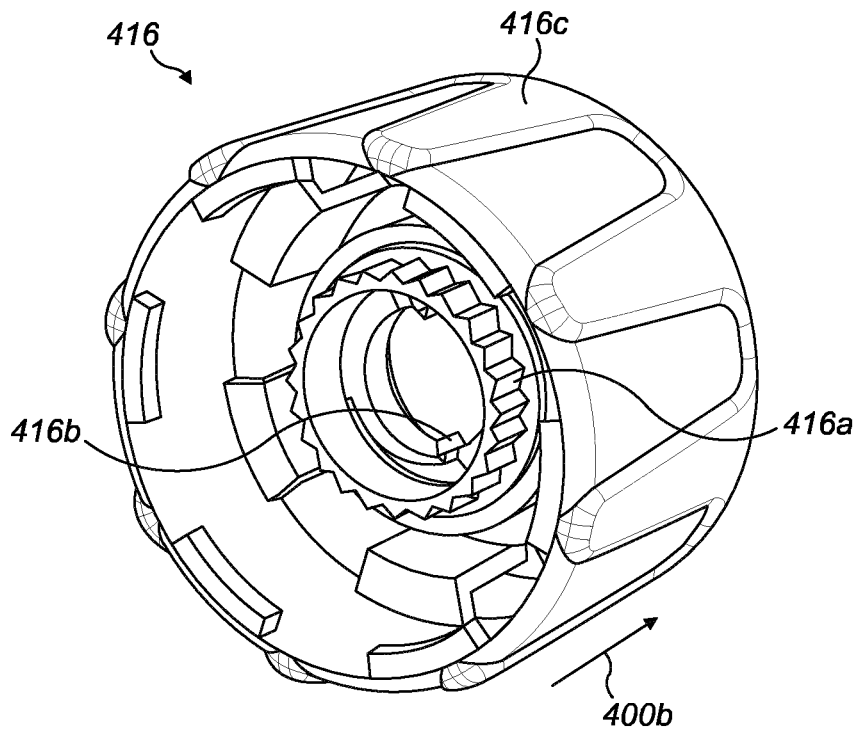
FIG. 4A is a perspective view of the dose selector, viewed from the front of the injection device.
Figure 4B:
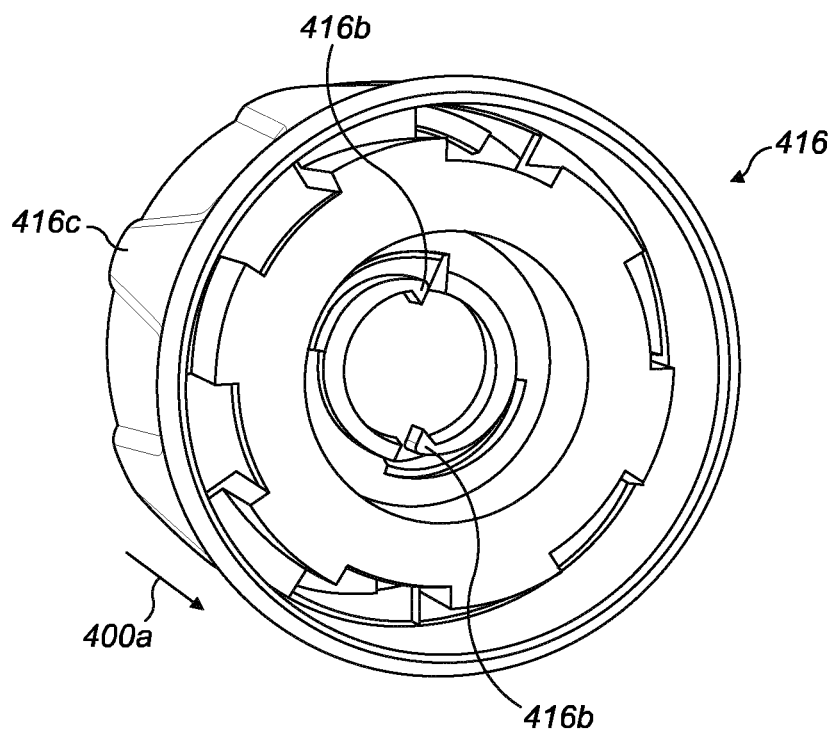
FIG. 4B is a perspective view of the dose selector, viewed from the rear of the injection device.

The dose selector 416 shown in FIGS. 4A and 4B includes a set of axially-extending splines 416a viewable from the front of the dose selector 416. These splines are involved in the disengagement of a hold ratchet arrangement. Viewable from the rear of the dose selector 416 are two ratchet pawls 416b, spaced 180 degrees apart. The ratchet pawls 416b are part of an over-torque feature. An external surface of the dose selector 416 is provided with a pattern of grip formations 416c to increase friction and to visually indicate to a user where to grip the injection device 400 in order to set the dose.

Figure 5A:
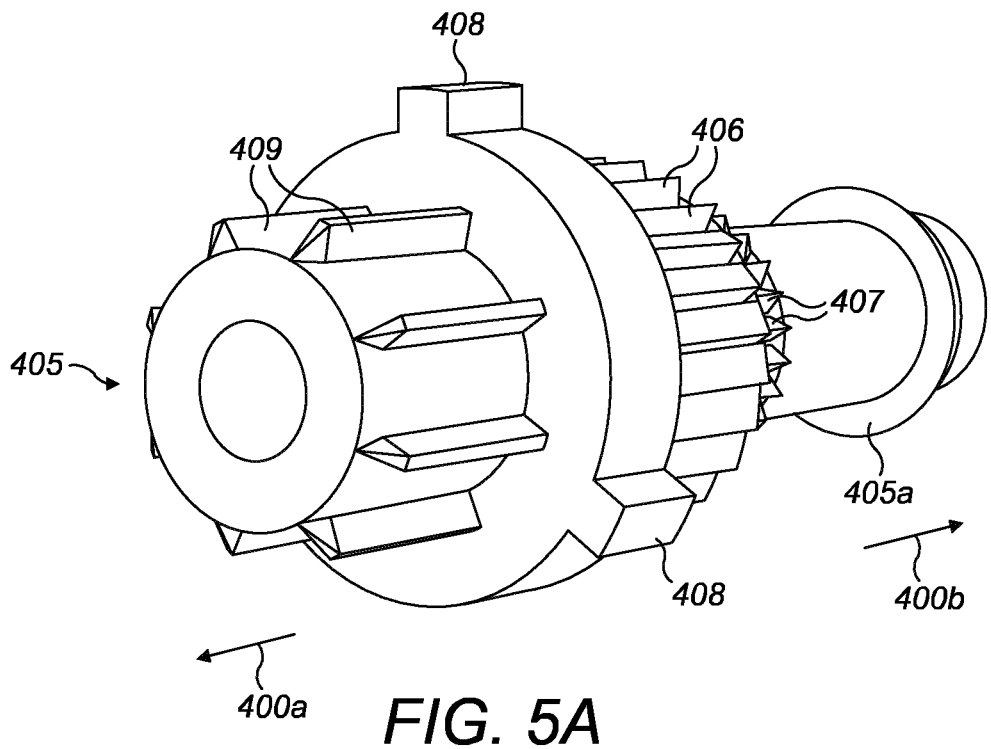
FIG. 5A is a perspective view of the drive plate, viewed from the front of the injection device.
Figure 5B:
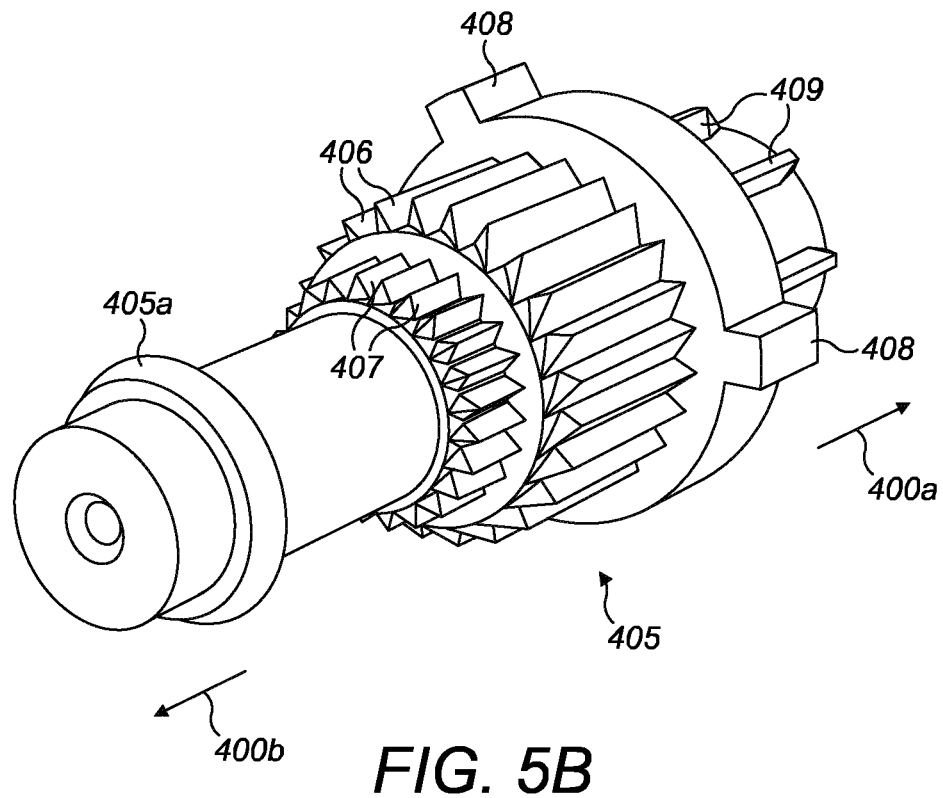
FIG. 5B is a perspective view of the drive plate, viewed from the rear of the injection device.

FIGS. 5A and 5B show the drive plate 405. The drive plate 405 includes a flange 405a for connecting the drive plate 405 to the dose button 430. Arranged axially along the drive plate 405 are four sets of splines. A first set of splines 406 forms part of the hold ratchet arrangement. Located axially rearwardly of the first set of splines 406 (i.e. towards the rear end 400b of the injection device 400) is a second set of splines 407. The second set of splines 407 has a smaller maximum diameter than the first set of splines 406.

At a region of the drive plate 405 having a maximum outer diameter is located a third set of three widely and equally-spaced splines 408 which are capable of engaging the drive sleeve 439.

At a front end of the drive plate 405 (i.e. towards the front end 400a of the injection device 400) is located a fourth set of splines 409 which are capable of engaging the drive shaft 440.

Figure 6A:
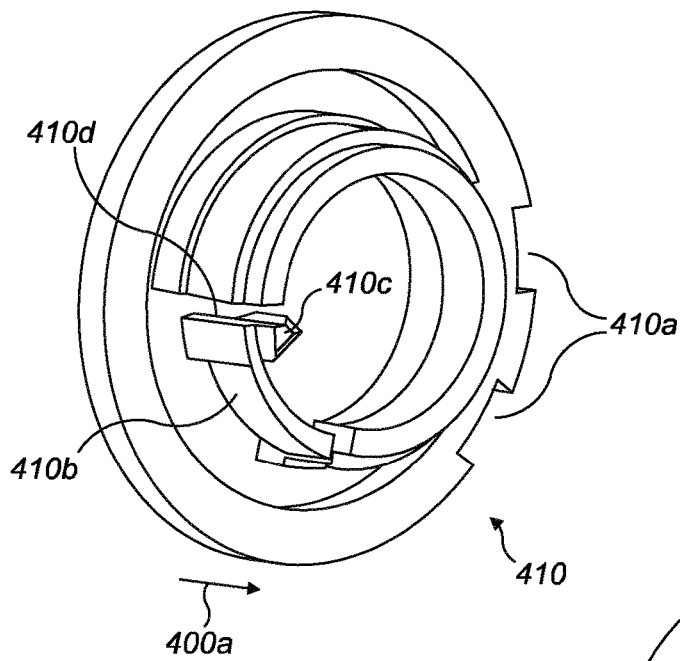
FIG. 6A is a perspective view of the ratchet ring, viewed from the front of the injection device.
Figure 6B:
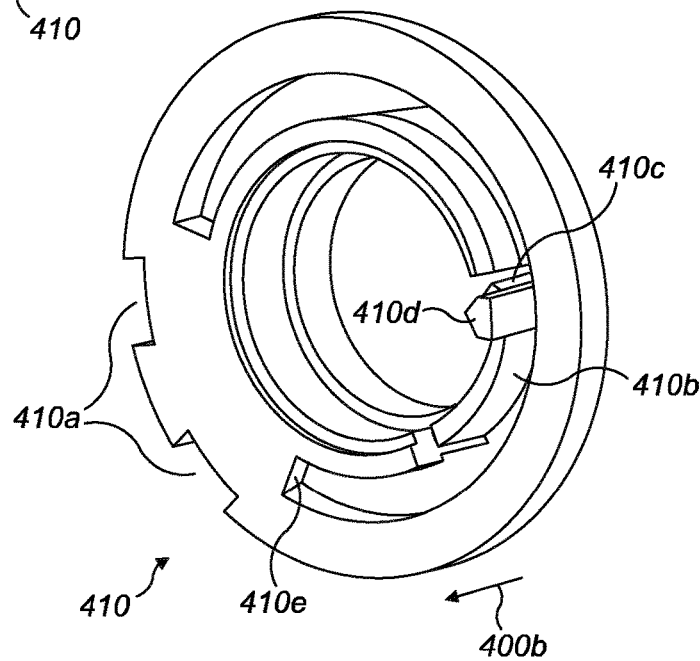
FIG. 6B is a perspective view of the ratchet ring, viewed from the rear of the injection device.
Figure 6C:
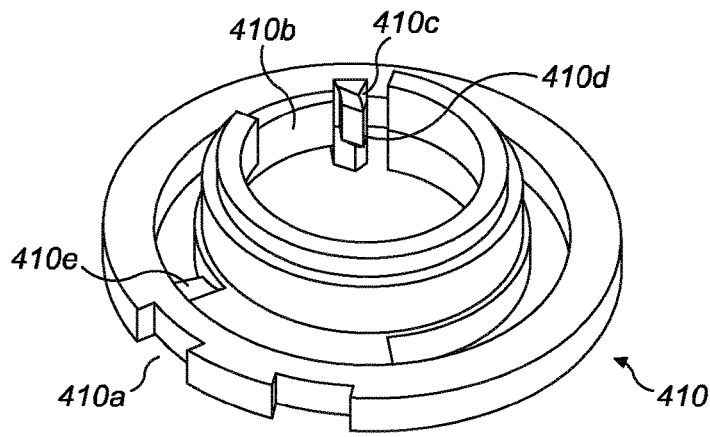
FIG. 6C is another perspective view of the ratchet ring.
Figure 7:
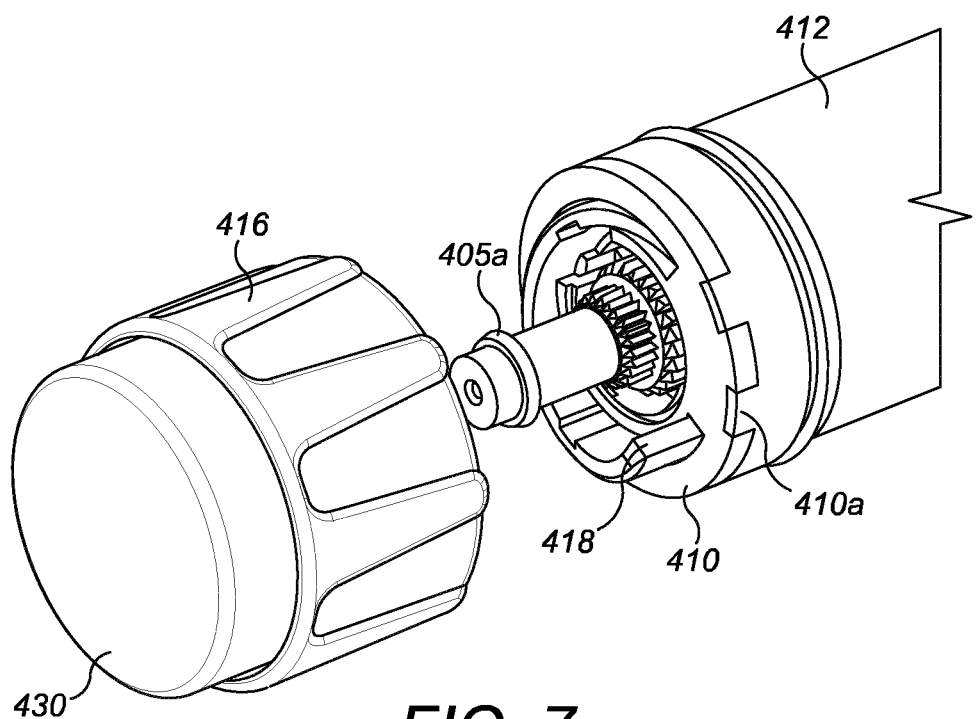
FIG. 7 is a perspective, partly-exploded view of the rear of the injection device.
Figure 8:
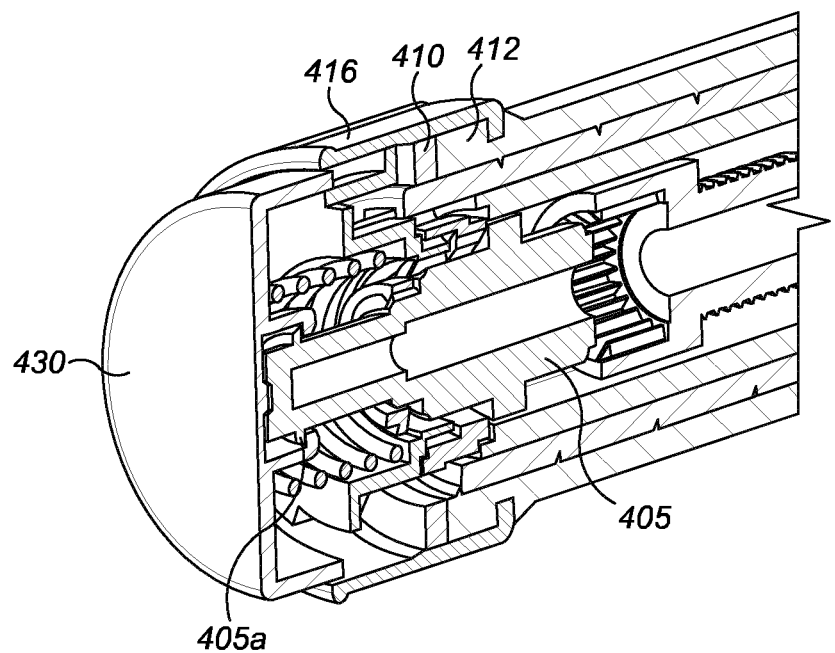
FIG. 8 is a cross-sectional view of the FIG. 7 components assembled together.

FIGS. 6A-6C show the ratchet ring 410. The ratchet ring 410 includes two notches 410a which engage corresponding formations on the housing 412 to lock the ratchet ring 410 axially and rotationally with respect to the housing 412 (FIG. 7). In an alternative embodiment the ratchet ring 410 could be formed as an integral part of the housing 412. As shown in FIG. 8, the ratchet ring 410 is held or arranged between or adjacent to the housing 412 and the dose selector 416. The ratchet ring 410 includes a hard rotary endstop 410e for the number sleeve 418.

The ratchet ring 410 includes a flexible ratchet arm 410b, at the end of which is a ratchet component in the form of two adjacent ratchet pawls 410c, 410d. The ratchet pawls 410c, 410d have different depths and/or angled surfaces so that, when the dose setting mechanism is assembled together, the ratchet pawl 410c is able to engage the first set of splines 406 on the drive plate 405 and the ratchet pawl 410d is able to engage the splines 416a on the dose selector 416.

Figure 11:
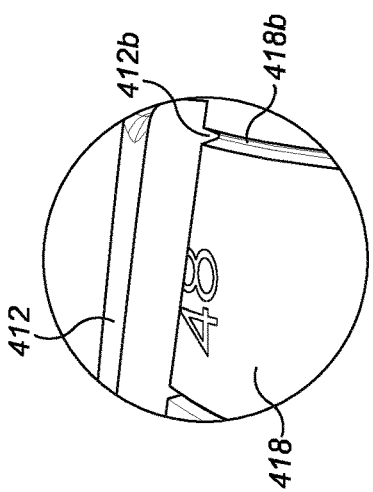
FIG. 11 is a perspective view of the number sleeve and housing assembled together.
Figure 10:
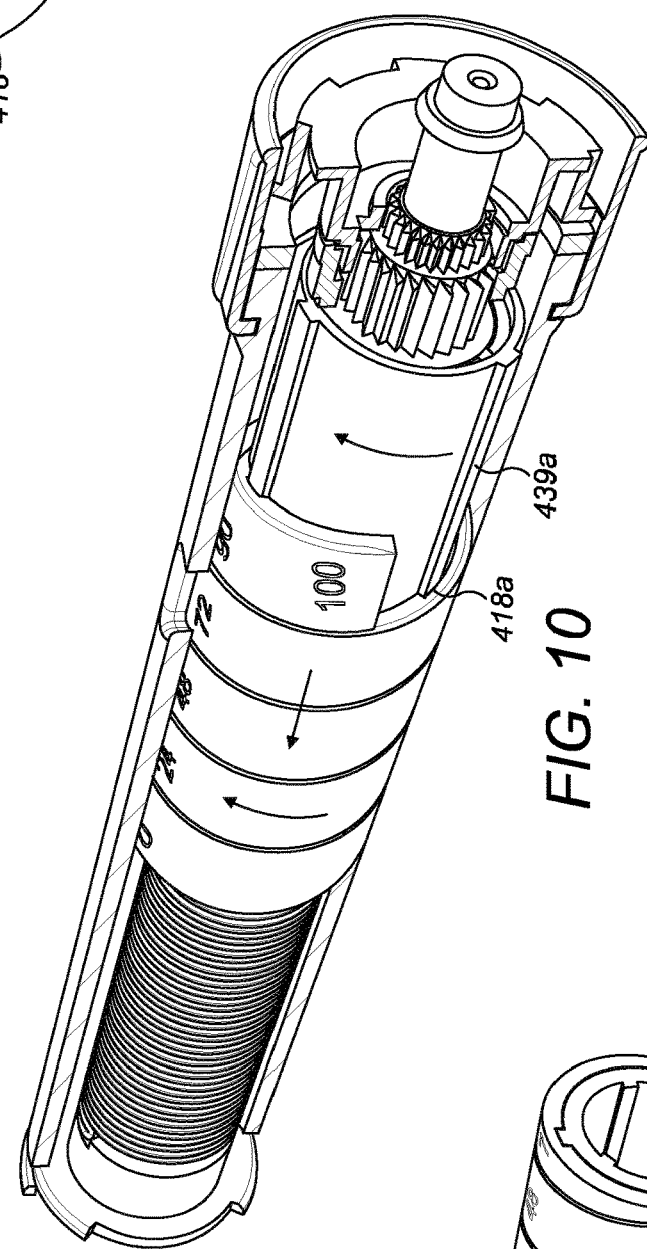
FIG. 10 is a perspective view, partly in cross-section, showing selected components of the injection device including the drive sleeve and number sleeve assembled together.
Figure 9:
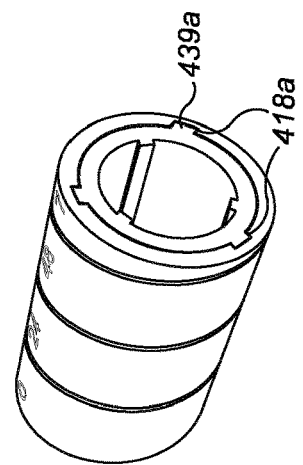
FIG. 9 is a perspective view of the drive sleeve and number sleeve assembled together.

Referring to FIGS. 9-11, the drive sleeve 439 has three equally spaced longitudinally extending external splines 439a which engage in longitudinal grooves 418a on an internal surface of the number sleeve 418. The number sleeve 418 can therefore move axially with respect to the drive sleeve 439 but is rotationally locked thereto.

An external surface of the number sleeve 418 has a helical groove 418b which engages with a thread 412b on an internal surface of the housing 412. The number sleeve 418 can therefore rotate with respect to the housing 412, guided by the thread 412b.

Figure 12A:
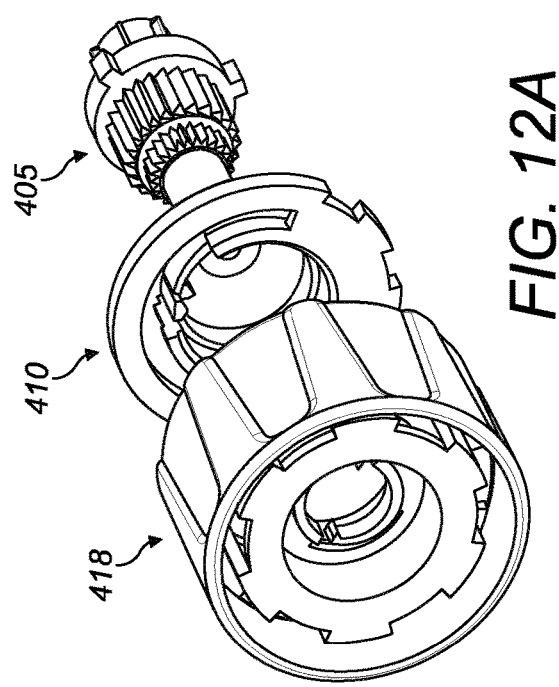
FIGS. 12A and 12B are an exploded view and an assembled view of the dose selector, ratchet ring and drive plate, viewed from the rear of the injection device.
Figure 12B:
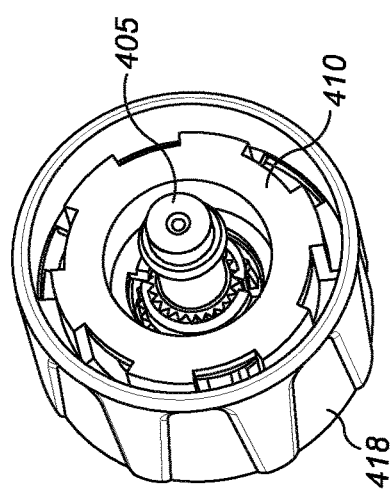

FIGS. 12A and 12B show an exploded view and an assembled view of the dose selector, ratchet ring and drive plate, viewed from the rear of the injection device.

Figure 13A:
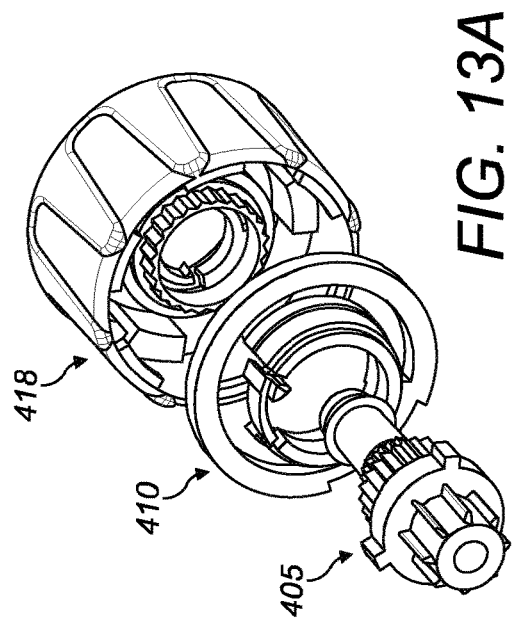
FIGS. 13A and 13B are an exploded view and an assembled view of the dose selector, ratchet ring and drive plate, viewed from the front of the injection device.
Figure 13B:
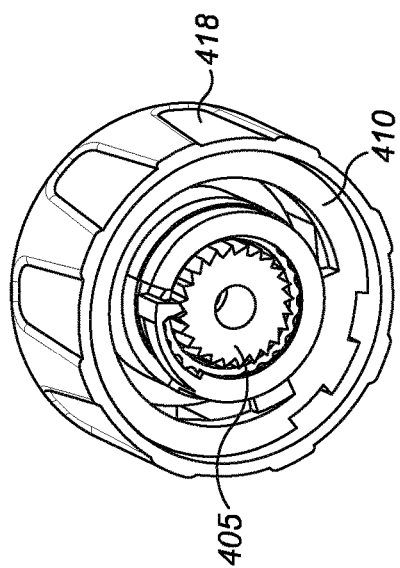

FIGS. 13A and 13B are an exploded view and an assembled view of the dose selector, ratchet ring and drive plate, viewed from the front of the injection device.

The operation of the respective features of the injection device 400 will now be described in more detail below.

Dose Setting—Incrementing the Dose

Figure 14A:
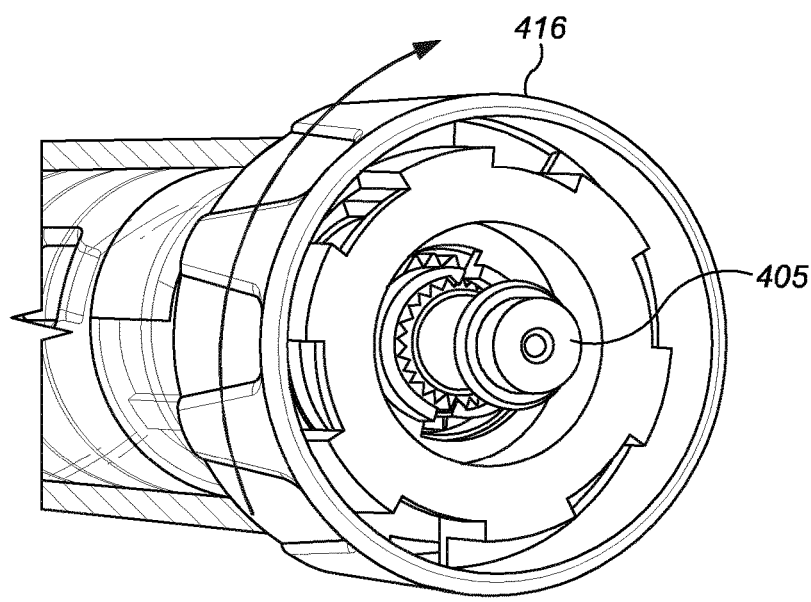
FIGS. 14A-14C, 15A and 15B illustrate incrementing the dose.
Figure 14B:
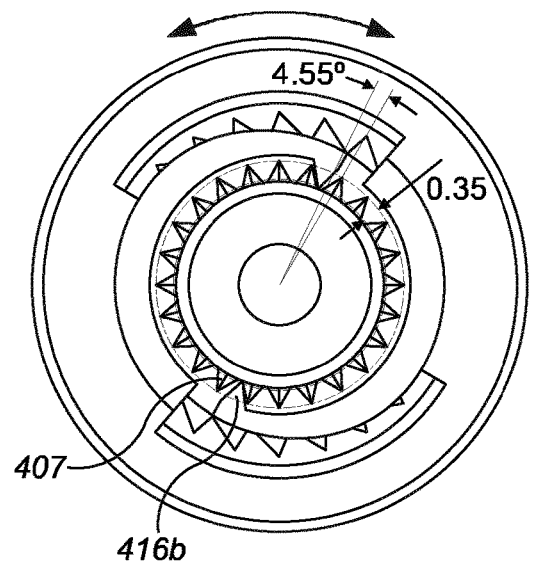
Figure 14C:
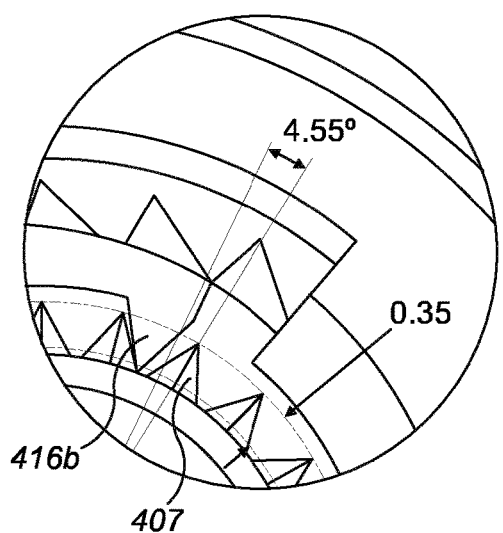

As shown in FIG. 14A, the user turns the dose selector 416 clockwise. After some degrees of unengaged rotation, preferably 3 to 7 degrees, most preferably between 4 to 5 degrees of unengaged rotation, in the embodiment 4.55° rotation, the dose selector ratchet pawl 416b starts to engage and drive the drive plate 405 clockwise via the second set of splines 407 on the drive plate 405 (FIG. 14B). The ratchet ring 410 is rotationally fixed or being integral to the housing 412 and does not rotate. The ratchet ring first pawl 410c is engaged with the drive plate splines 406 in order to provide a hold ratchet arrangement.

Figure 15A:
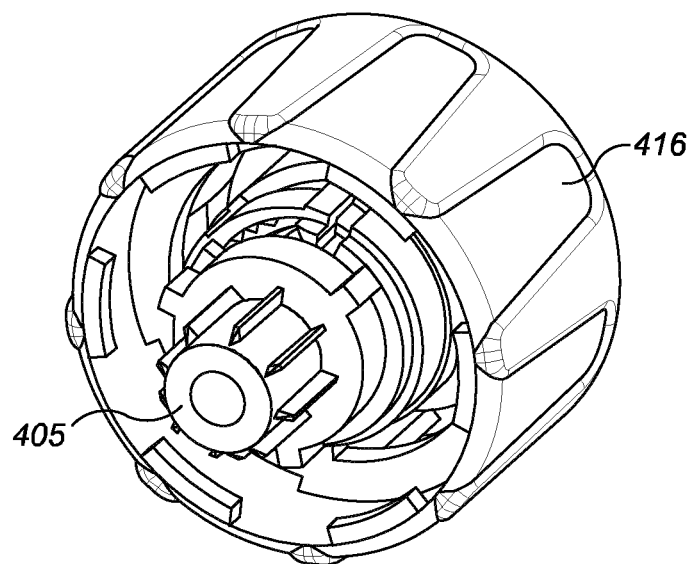
Figure 15B:
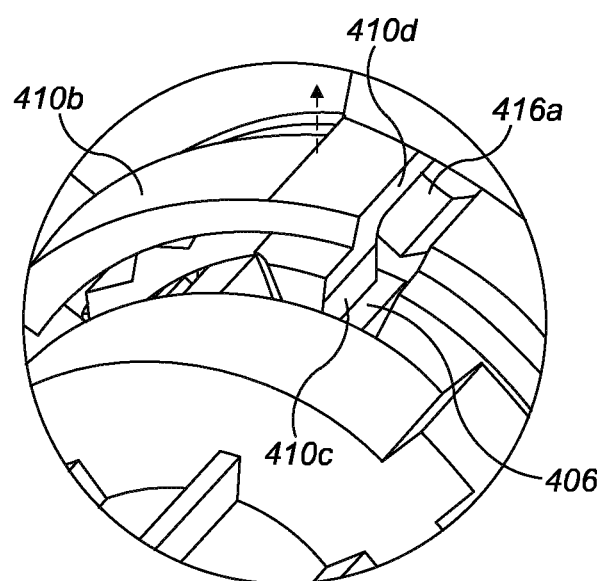

As shown in FIG. 15B the dose selector disengagement splines 416a push against the ratchet ring second pawl 410d to disengage the hold ratchet. This is shown in more detailed steps in FIGS. 16A-16E.

Figure 16C:
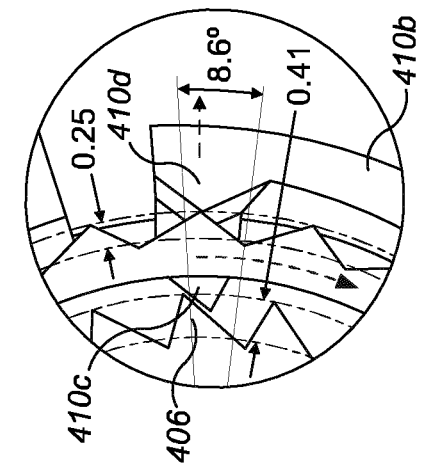
FIGS. 16A-16E illustrate the dose incrementing stages in more detail.
Figure 16E:
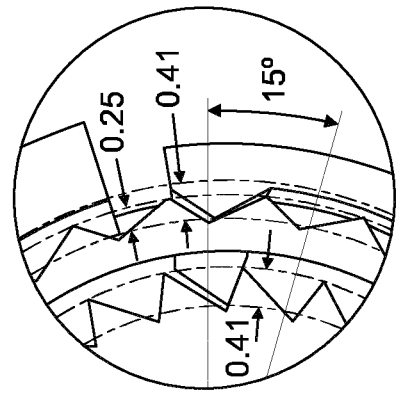
Figure 16B:
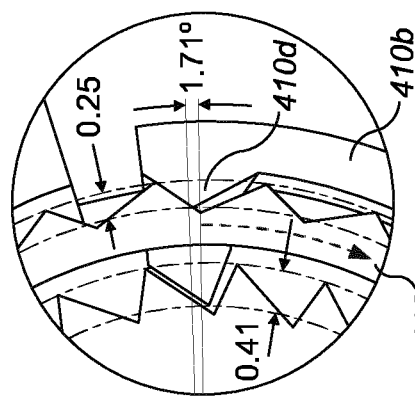
Figure 16D:
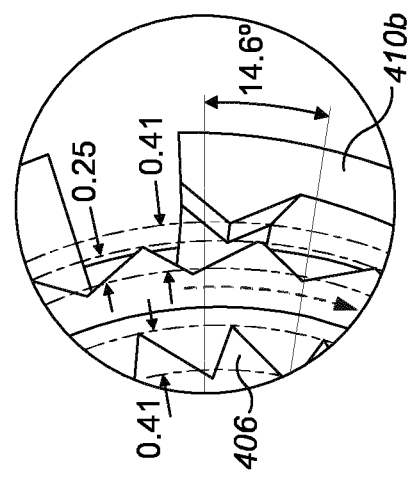
Figure 16A:
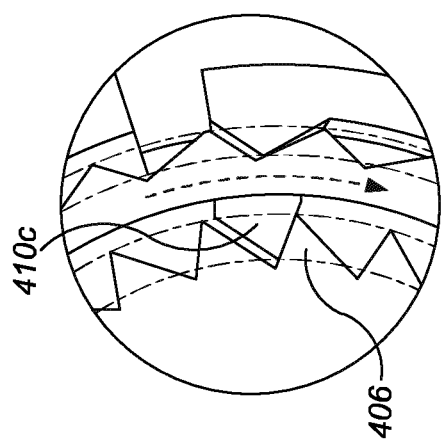
Figure 17A:
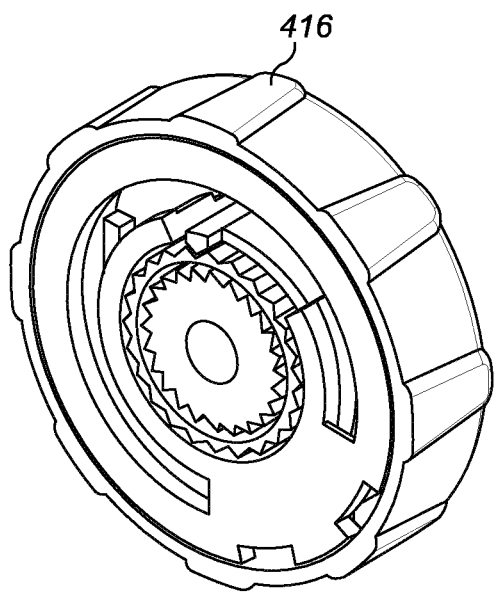
FIGS. 17A-17C are further views illustrating incrementing the dose.
Figure 17B:
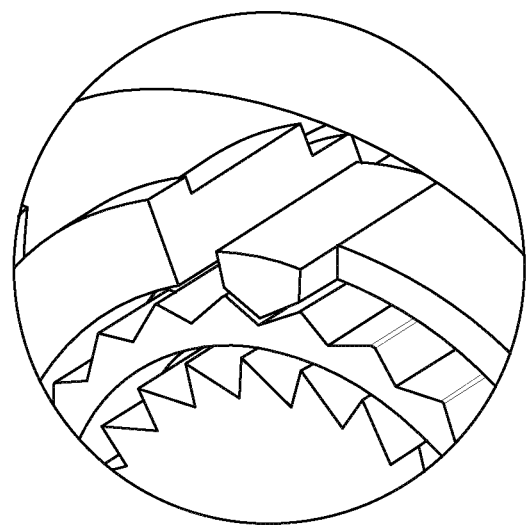
Figure 17C:
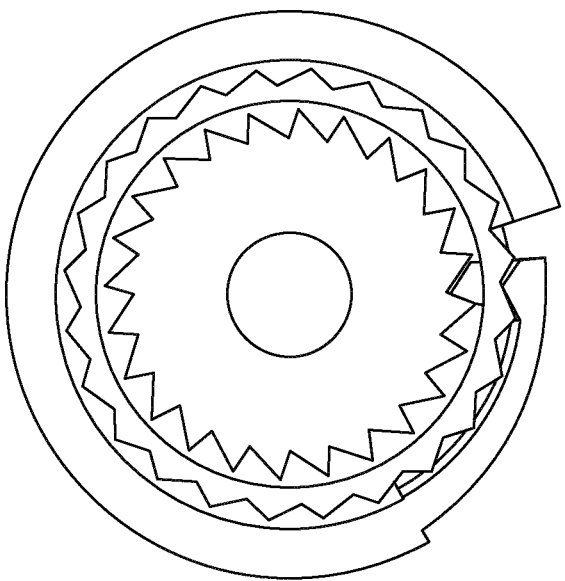
Figure 18:
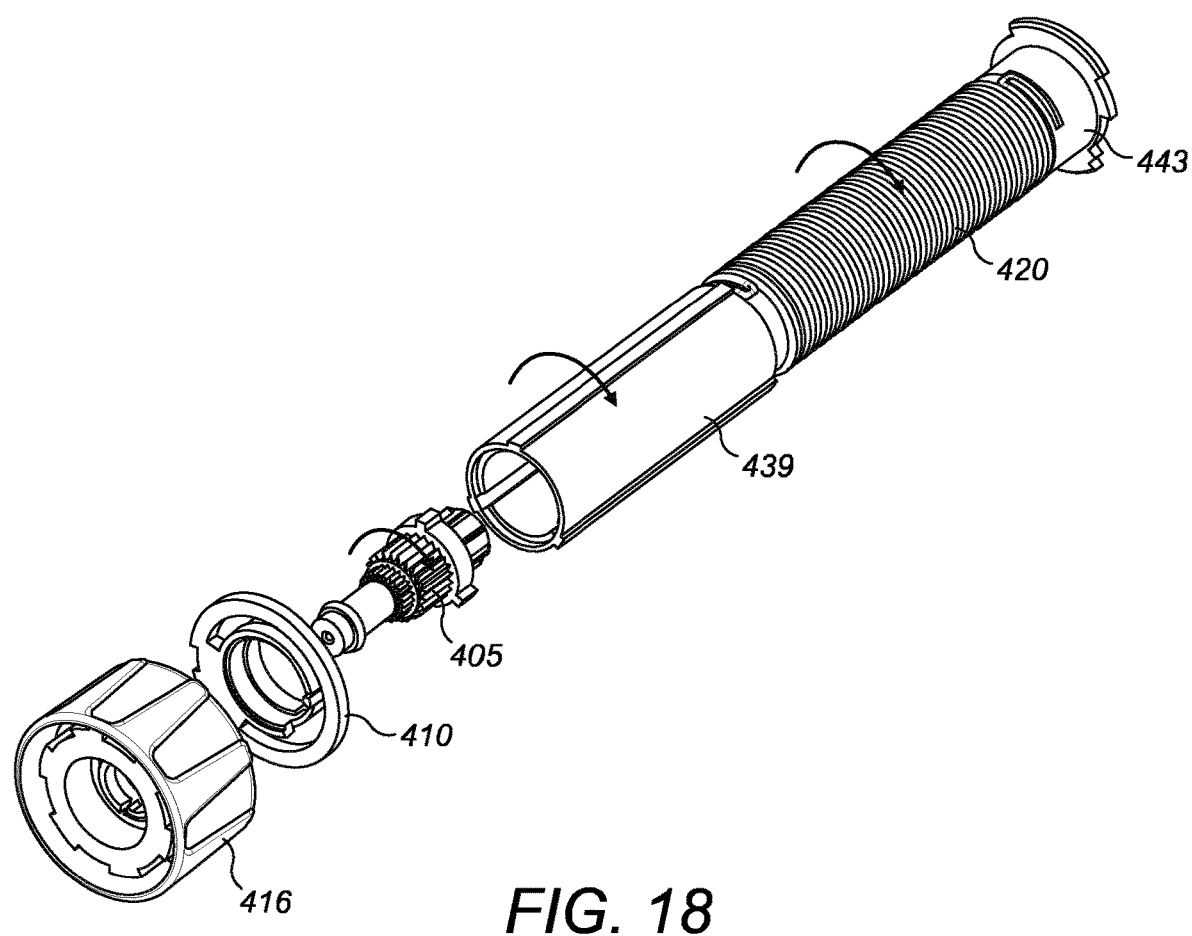
FIG. 18 is an exploded view of components involved in incrementing the dose.

Stored energy in the drive spring 420 causes the drive plate splines 406 to push against the first pawl 410c of the ratchet ring 410 hold ratchet arrangement (FIG. 16A).

As the dose selector 416 is rotated, the dose selector splines 416a start to engage the second pawl 410d of the ratchet ring 410. A first rotation of 1 to 3 degrees, in the embodiment 1.7° of rotation does not move the pawl 410d, or the ratchet arm 410b to which it is attached (FIG. 16B).

When the dose selector 416 has been rotated 5 to 12 degrees, preferably between 7 to 10 degrees, in the embodiment 8.6° (FIG. 16C), the dose selector splines 416a have pushed the pawl 410d and ratchet arm 410b radially outwardly by 0.1 mm to 1 mm, in the embodiment 0.25 mm so that the pawl 410d disengages from the dose selector splines 416a. The hold ratchet is still engaged, however, because the first ratchet ring pawl 410c is still engaged with the drive plate splines 406.

For the last part of the turn, when the dose selector 416 has been rotated 10 to 20 degrees, preferably between 13 to 17 degrees, in the embodiment 14.6° ((FIG. 16D) the drive plate splines 406 push the first pawl 410c, causing the ratchet arm 410b to move radially outwardly to 0.3 mm to 1.5 mm, in the embodiment 0.41 mm. The hold ratchet temporarily disengages as the first pawl 410c disengages from the drive plate splines 406.

When the dose selector 416 has been rotated more than 10 to 20 degrees, preferably more than 13 degrees, in the embodiment 15° the ratchet arm 410b clicks over into the next splines i.e. the first pawl 410c engages the next drive plate spline 406 and the second pawl 410d engages the next dose selector spline 416a. This produces haptic feedback for the user and re-engages the hold ratchet (FIG. 16E), whereupon the process can be repeated if the dose is to be incremented further.

Figure 19:
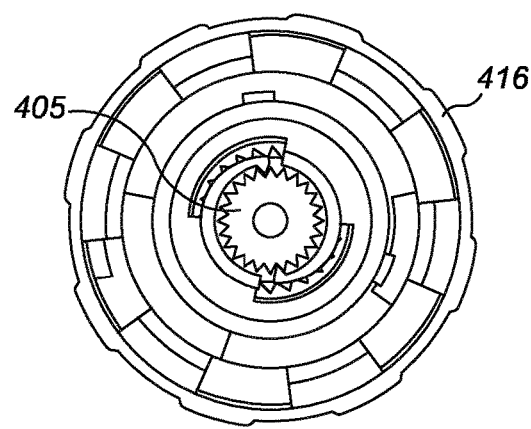
FIG. 19 is a cross-sectional view of the dose selector and dose plate.
Figure 20:
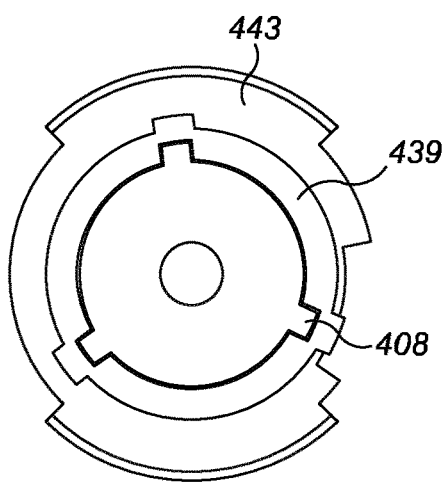
FIG. 20 is a cross-sectional view of the dose plate, drive sleeve and chassis.
Figure 21:
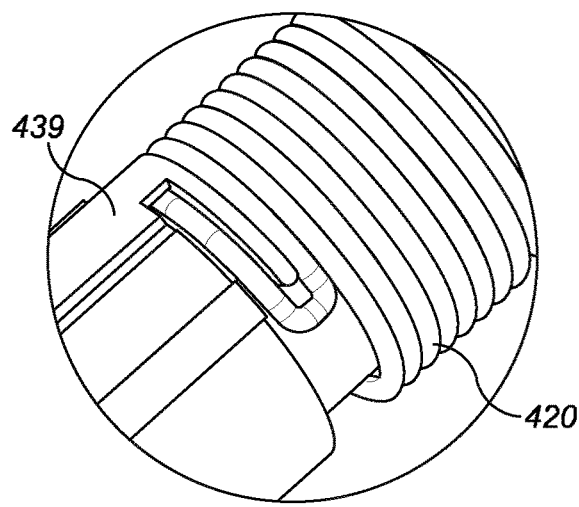
FIG. 21 shows one end of the drive spring attached to the drive sleeve.
Figure 22:
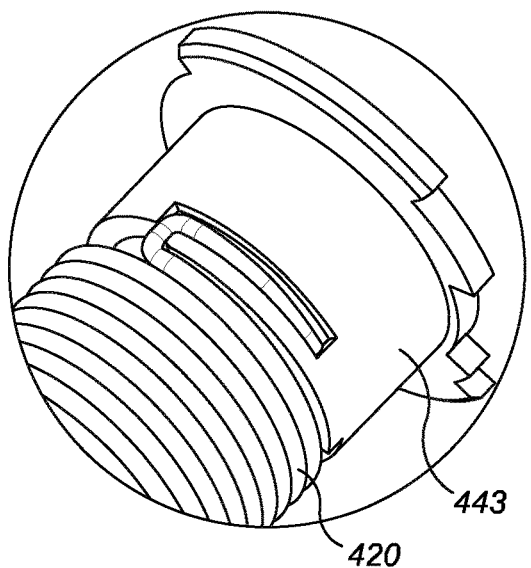
FIG. 22 shows the other end of the drive spring attached to the chassis.

As the dose selector ratchet pawl 416b drives the drive plate 405 clockwise (FIG. 19), the drive plate 405 rotates the drive sleeve 439 by virtue of the third set of drive plate splines 408 (FIG. 20). The drive sleeve 439 is locked to the drive spring 420, winding (and therefore charging) the spring 420 as the drive sleeve 439 turns (FIG. 21). The drive spring 420 is fixed at its other end to the chassis 443 (FIG. 22).

Figure 23A:
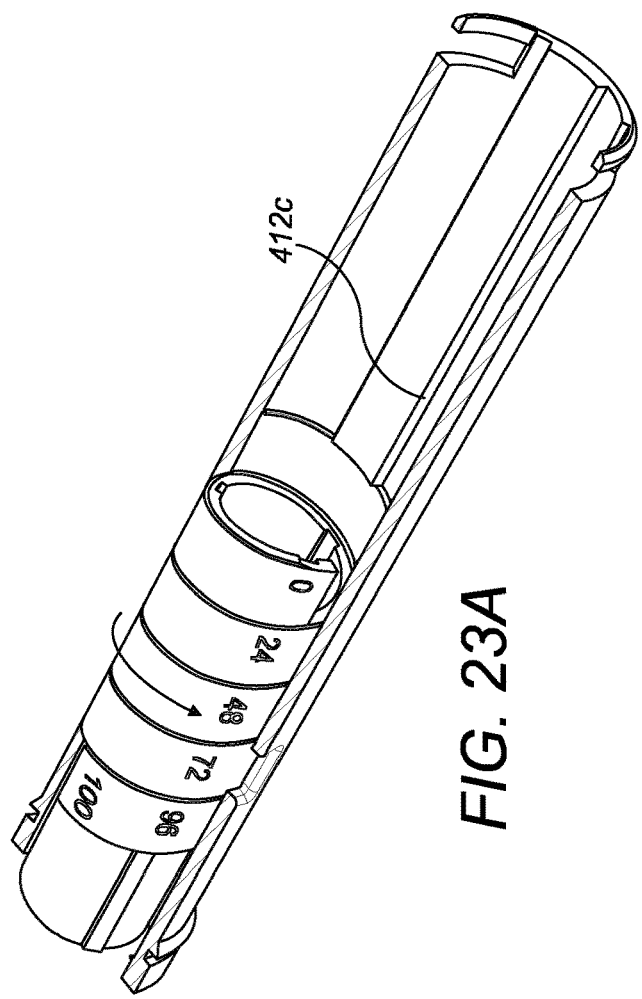
FIGS. 23A and 23B show how the number sleeve reaches the endstop in the housing.
Figure 23B:
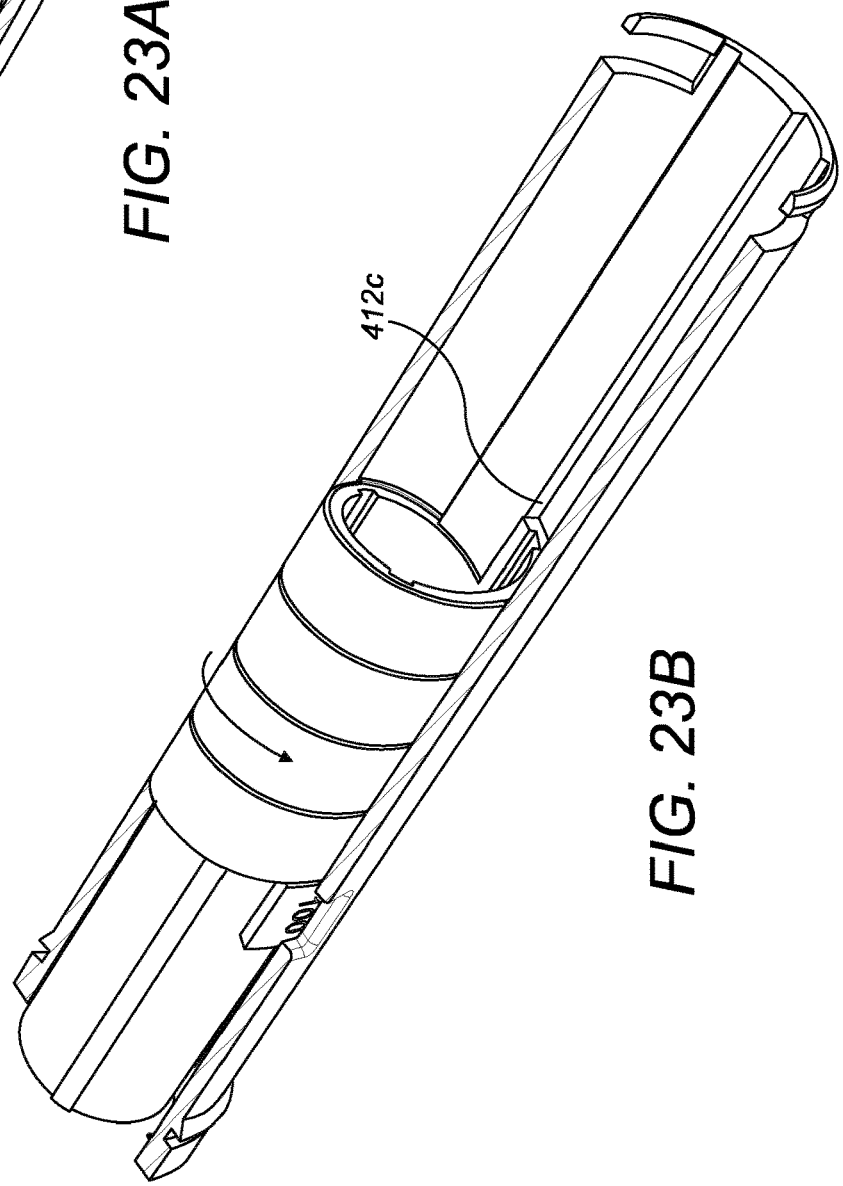

As the drive sleeve 439 turns, it turns the number sleeve 418 by virtue of the external drive sleeve splines 439a (FIG. 10). As the number sleeve 418 turns, it advances along the thread 412b on the internal surface of the housing 412 (FIG. 11). The number sleeve 418 cannot advance further than a hard endstop 412c on an internal surface of the housing 412 which prevents further rotation of the number sleeve 418 (FIG. 23B).

Dose Setting—Decrementing the Dose

Figure 24A:
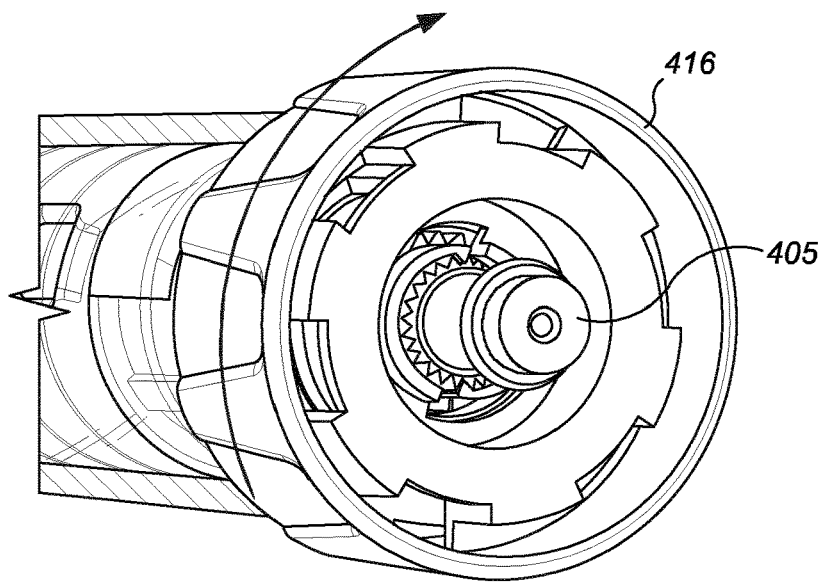
FIGS. 24A-24C, 25A and 25B illustrate decrementing the dose.
Figure 24B:
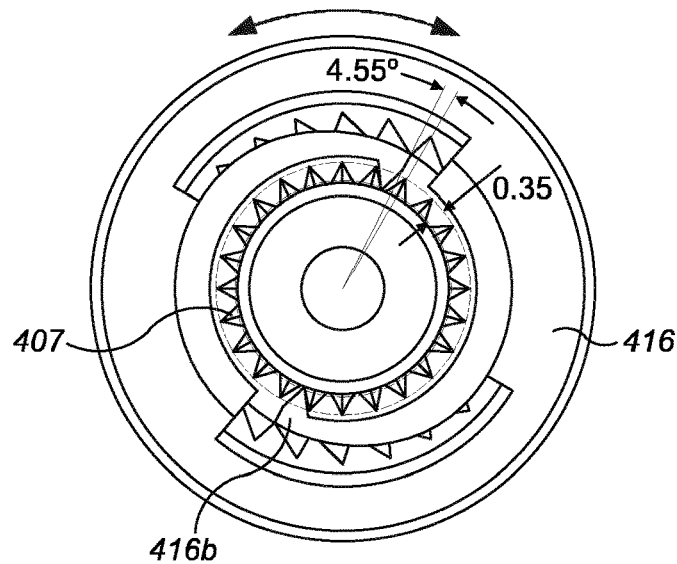
Figure 24C:
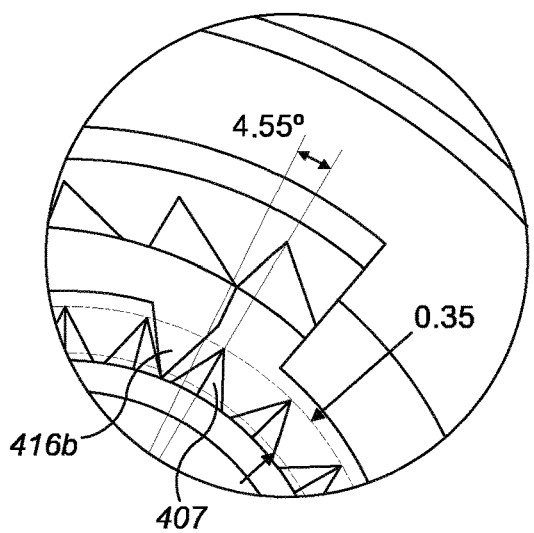
Figure 25A:
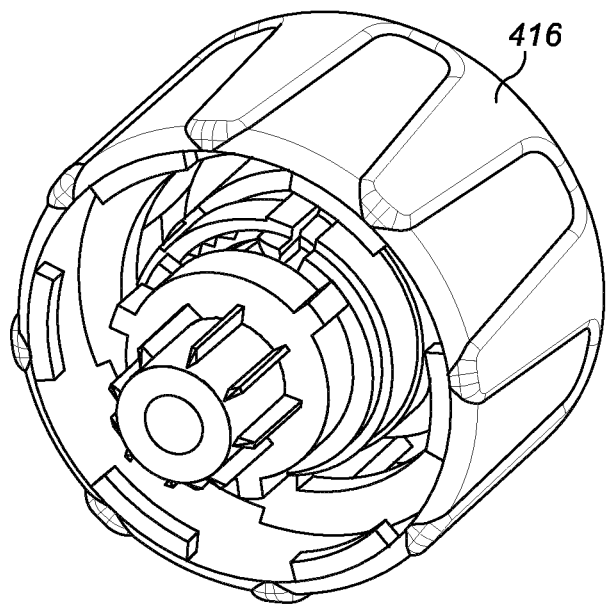
Figure 25B:
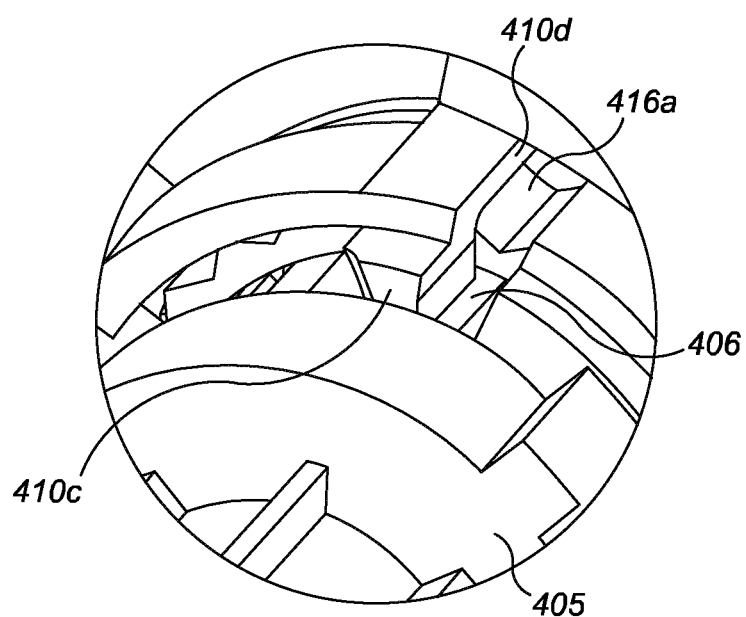

To decrement the dose, the user turns the dose selector 416 anti-clockwise (FIG. 24A). As the dose selector 416 is turned anti-clockwise, there is a small amount of lost motion such that the dose selector 416 rotates slightly, preferably between 1 to 8 degrees relative to the ratchet pawl 416b. In the specific embodiment, after 3.8° of rotation, the hold ratchet will disengage and the dose selector ratchet pawl 416b can start to drive the drive plate 405 anti-clockwise via the second set of splines 407 on the drive plate 405 (FIG. 24C). The ratchet ring 410 is rotationally fixed to the housing 412 and does not rotate.

Figure 26C:
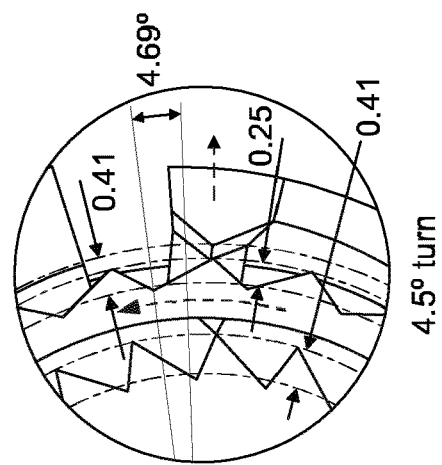
FIGS. 26A-26E illustrate the dose decrementing stages in more detail.
Figure 26B:
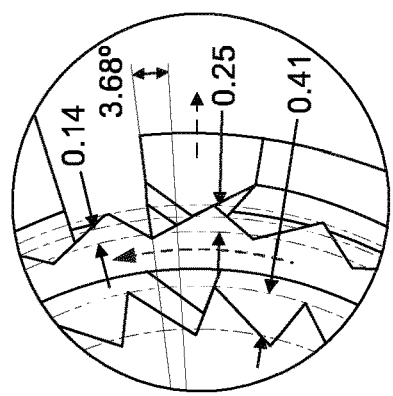
Figure 26A:
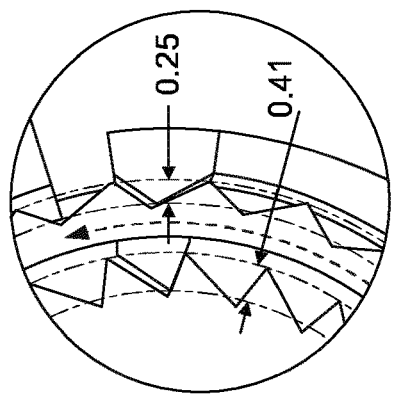

Initially, the ratchet ring first pawl 410c is engaged with the drive plate splines 406 and the ratchet ring second pawl 410d is engaged with the dose selector splines 416a so as to provide the hold ratchet arrangement (FIG. 26A). The splines 406, 416a are pushing against the pawls 410c, 410d as a result of the stored energy in the drive spring 420.

As the dose selector 416 is turned anti-clockwise, the first 1 to 5 degrees, in the embodiment 3.7° of rotation pushes the ratchet arm 410b 0.1 mm to 0.5 mm in the specific embodiment 0.14 mm radially outwardly (FIG. 26B).

After 3 to 6 degrees, in the embodiment 3.7° of rotation, the drive plate 405 starts to turn with the dose selector 416, further disengaging the hold ratchet and allowing the drive plate 405 to turn (FIG. 26C).

Figure 26E:
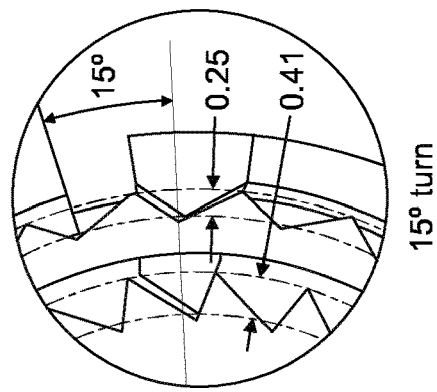
Figure 26D:
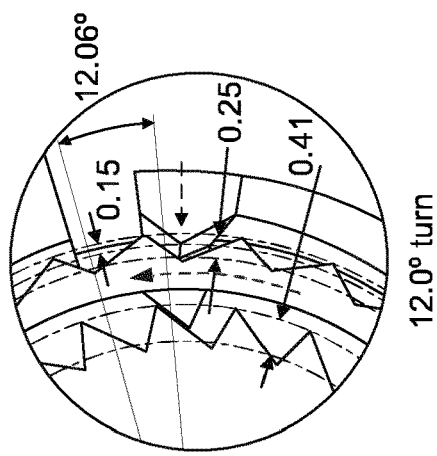
Figure 27A:
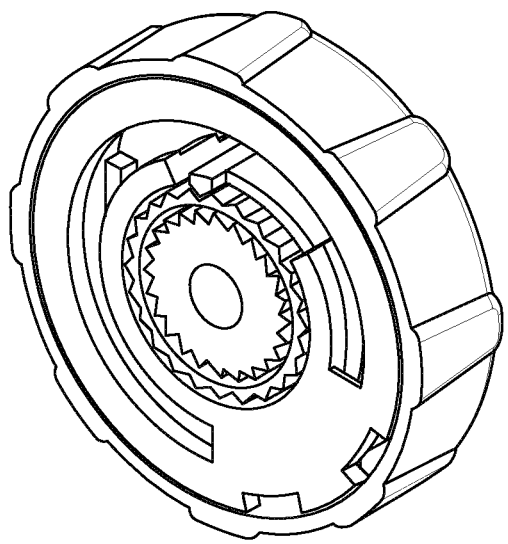
FIGS. 27A-27C are further views illustrating decrementing the dose.
Figure 27B:
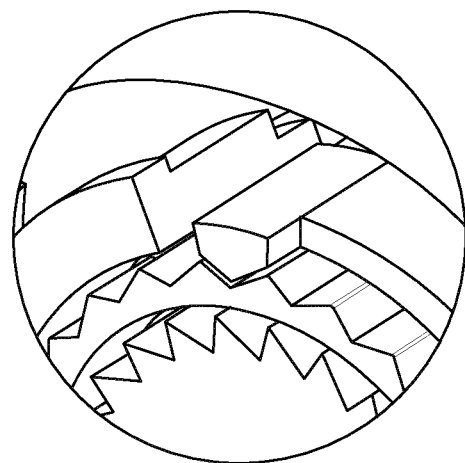
Figure 27C:
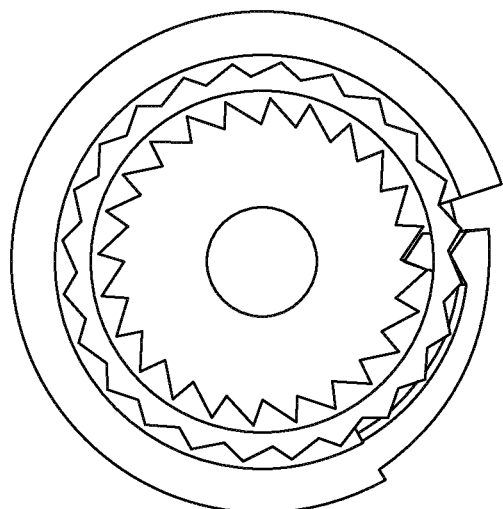

The hold ratchet then re-engages; the pawls 410c, 410d catching on the next splines 406, 416a and providing haptic feedback (FIG. 26D).

Once the hold ratchet has re-engaged, the process can be repeated if the dose is to be decremented further (FIG. 26E).

The dose decrementing process is summarised in FIG. 28, in which it can be seen that the dose selector 416 turns the drive plate 405. The drive plate 405 turns the drive sleeve 439. The drive sleeve 439 turns the drive spring 420 to discharge it and also turns the last dose nut 441 and the number sleeve 418.

Figure 29A:
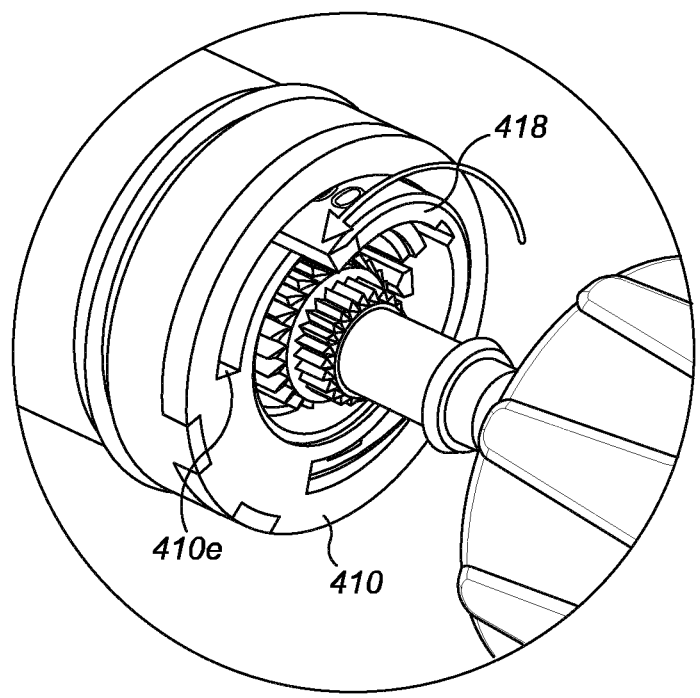
FIGS. 29A and 29B show how the number sleeve reaches the endstop in the ratchet ring.
Figure 29B:
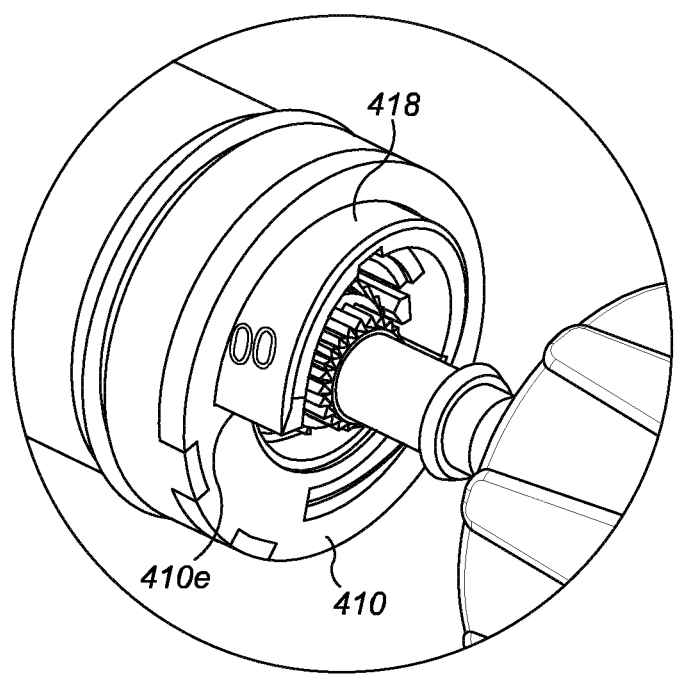

The number sleeve 418 will progress backwards, decrementing the indicated dose, until it reaches the hard rotary endstop 410e on the ratchet ring 410 (FIG. 29B).

Dose Setting-Over-Torque

Figure 30A:
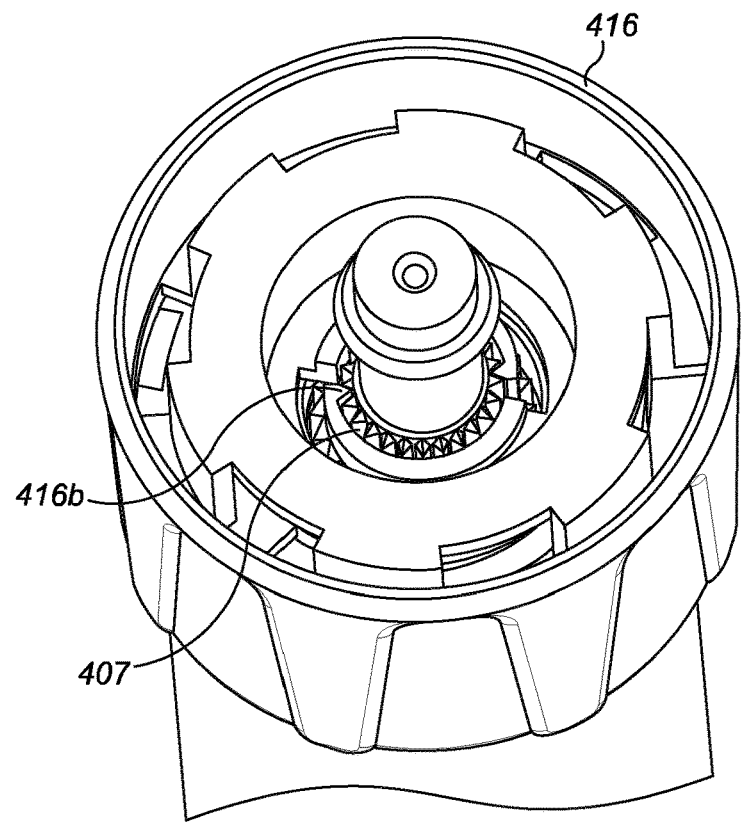
FIGS. 30A and 30B illustrate the over-torque feature.
Figure 30B:
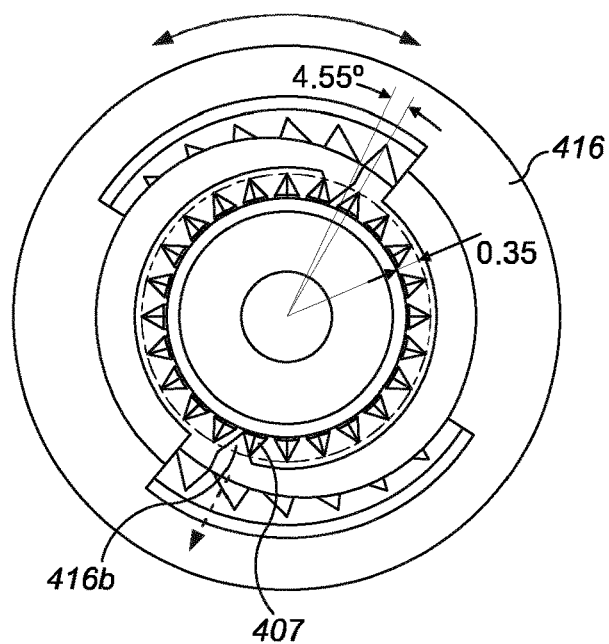

An over-torque feature is illustrated in FIGS. 30A and 30B. The over-torque feature is in the form of a ratchet arrangement is provided by the dose selector ratchet pawls 416b and the second set of splines 407 on the drive plate 405. If the number sleeve 418 has reached the endstop 410e or if the last dose protection (see below) is engaged, the over-torque feature protects components from potential damage caused by continued turning of the dose selector 416 by the user. The ratchet pawls 416b are displaced radially outwardly by 0.35 mm to disengage them from the splines 407, clicking over them to reduce the charging force transferred from the dose selector 416 to the drive spring 420. The over-torque for actuating the over-torque protection is preferably at least 10% higher than the torque required for dialling up (incrementing) or dialling down (decrementing) the dose selector 416. The dialling up torque can be 30 to 80 Nmm, preferably less than 60 Nmm, more preferably 30 to 50 Nmm. The dialling down torque can be 20 to 60 Nmm, preferably less than 50 Nmm, more preferably 30 to 40 Nmm. The over-torque in the dialling up direction may be different to the over-torque in dialling down direction.

Last Dose Protection

Last dose protection is provided by the last dose nut 441, as illustrated in FIGS. 31-33. As the drive sleeve 439 turns, it turns the last dose nut 441 which is splined thereto. This causes the last dose nut 441 to travel axially rearwardly along the drive shaft 440 to which it is threaded. The drive shaft 440 itself does not rotate during dose setting because it is rotationally locked to the chassis 443 via the chassis ratchet 442.

The last dose nut 441 moves axially 0.5 mm to 1 mm, preferably about 0.7 mm each turn. After 13.166 turns (representing 3161 U of medicament) the last dose nut 441 has moved sufficiently so that its endstop 441b has reached the hard rotary endstop 440a on the drive shaft 440. The last dose protection is now engaged and further incrementing of the dose is no longer possible.

Dose Delivery

Figure 34:
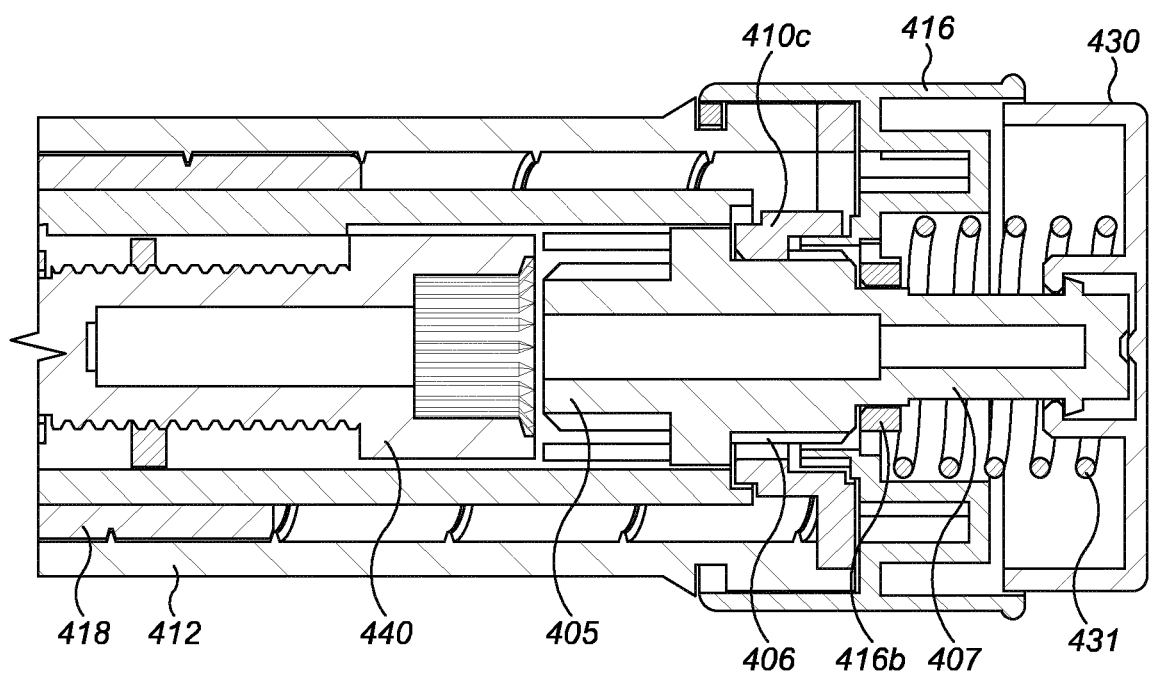
FIG. 34 shows the rear of the injection device ready to deliver a dose of medicament.

FIG. 34 shows the rear of the injection device 400 ready to deliver a dose of medicament. The dose button 430 is biased rearwardly by the dose button spring 431 and has not yet been pressed. The hold ratchet is engaged, i.e. the ratchet ring first pawl 410c is engaged with the first set of splines 406 on the drive plate 405. The over-torque feature is also engaged, i.e. the dose selector ratchet pawls 416b are engaged with the second set of splines 407 on the drive plate 405.

Figure 35A:
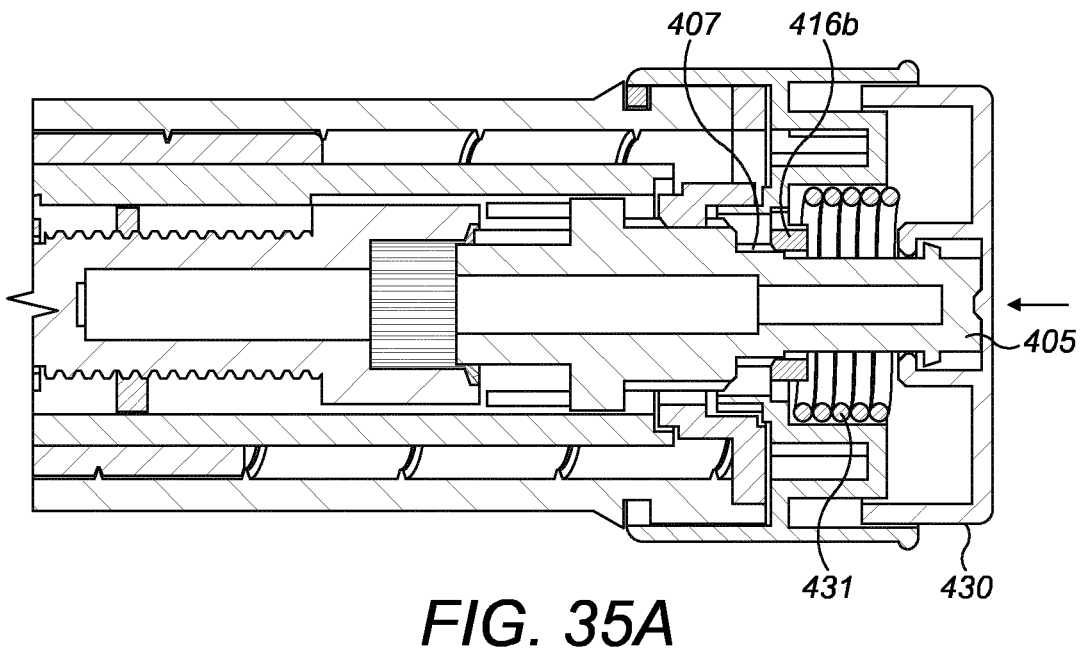
FIGS. 35A and 35B show the rear of the injection device shortly after the dose button has been pressed.
Figure 35B:
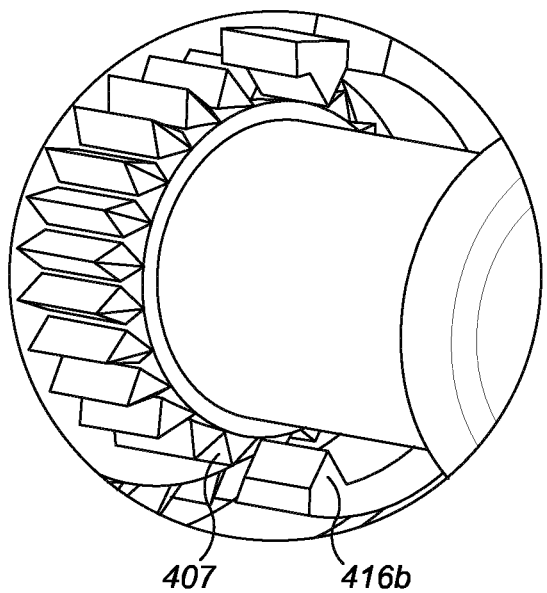

As the dose button 430 is axially depressed against the bias of the dose button spring 431 (FIG. 35A), the drive plate 405 is moved axially forward by the dose button 430 which is engaged with the rear of the drive plate 405. The forward axial movement of the drive plate 405 means that the dose selector ratchet pawls 416b (which have not moved axially) are no longer engaged with the splines 407, thus the over-torque feature is disengaged and the drive plate 405 is free of the dose selector 416 (FIG. 35B).

Figure 36A:
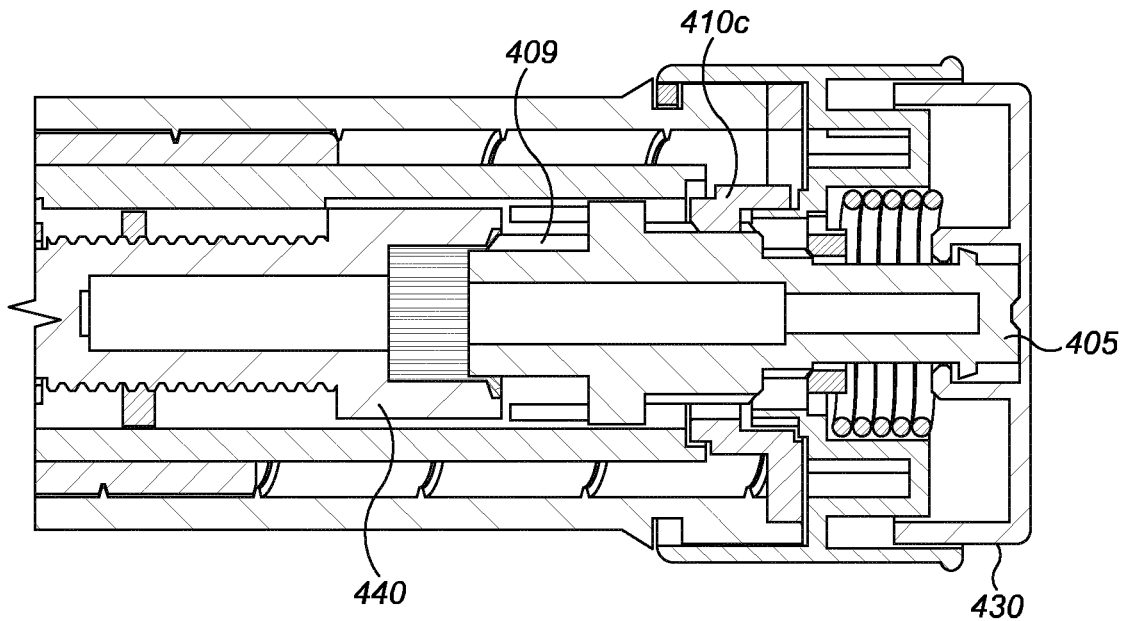
FIGS. 36A and 36B show the rear of the injection device after further pressing of the dose button, with the hold ratchet still engaged.
Figure 36B:
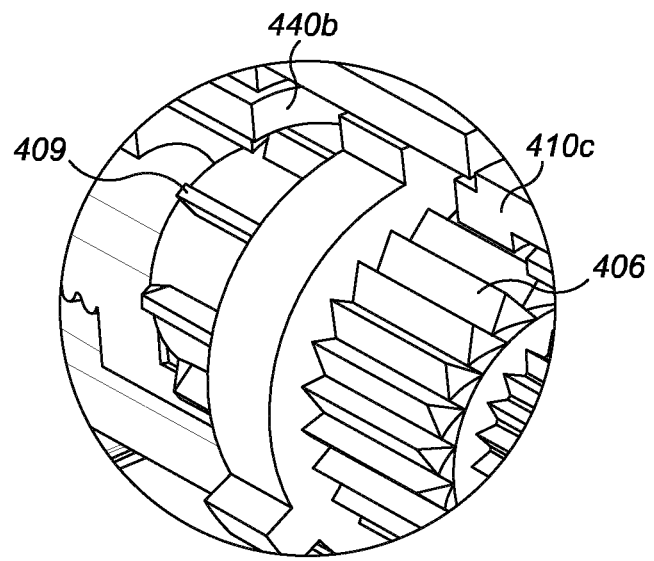

Further pressing of the dose button 430 causes continued forward axial movement of the drive plate 405. The fourth set of splines 409, at the front of the drive plate 405, begin to engage the internal splines 440b at the rear of the drive shaft 440 (FIGS. 36A and 36B). The drive plate splines 409 and drive shaft splines 440b operate together as a "drive clutch". At this point, the hold ratchet is still engaged (i.e. the ratchet ring first pawl 410c is still engaged with the first set of splines 406 on the drive plate 405) and the drive plate 405 is not yet able to rotate.

Figure 37A:
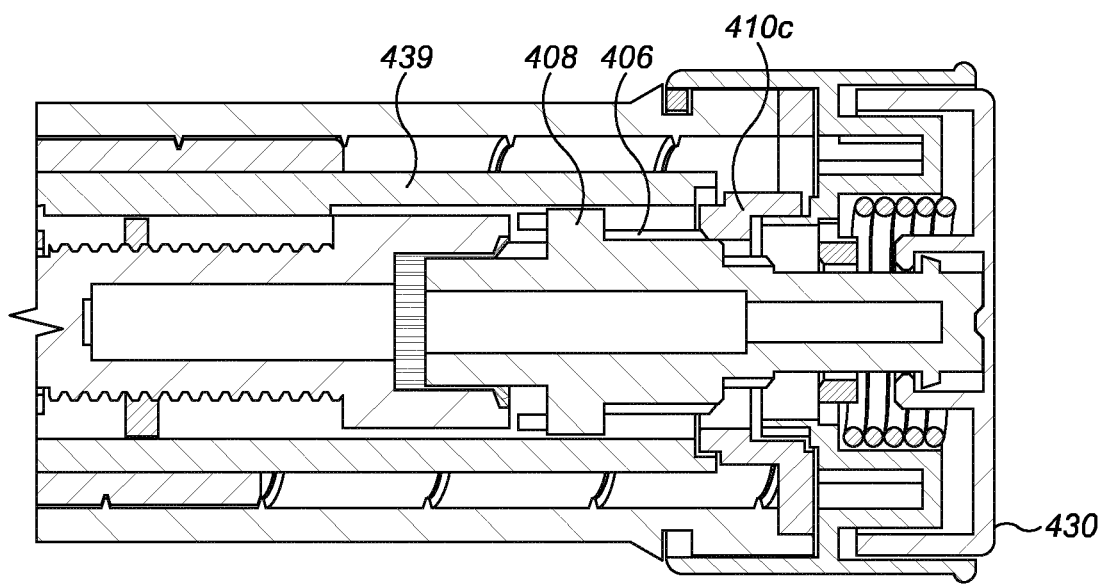
FIGS. 37A and 37B show the rear of the injection device after further pressing of the dose button, with the hold ratchet just released.
Figure 37B:
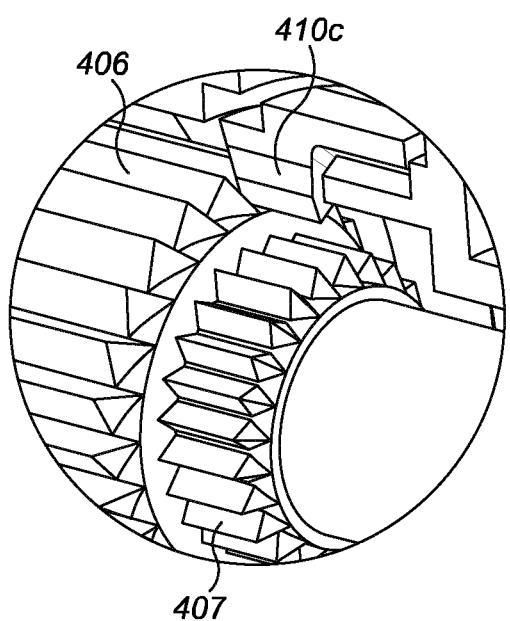

With reference to FIGS. 37A and 37B, further pressing of the dose button 430 causes continued forward axial movement of the drive plate 405. The hold ratchet is disengaged so that the drive plate splines 406 are now free of the ratchet ring pawl 410c and the drive plate 405 is free to rotate. The drive plate 405 is urged to rotate, driven by the drive sleeve 439 (FIG. 21) to which it is splined (via splines 408), the drive sleeve 439 being driven by the charged drive spring 420.

Figure 38A:
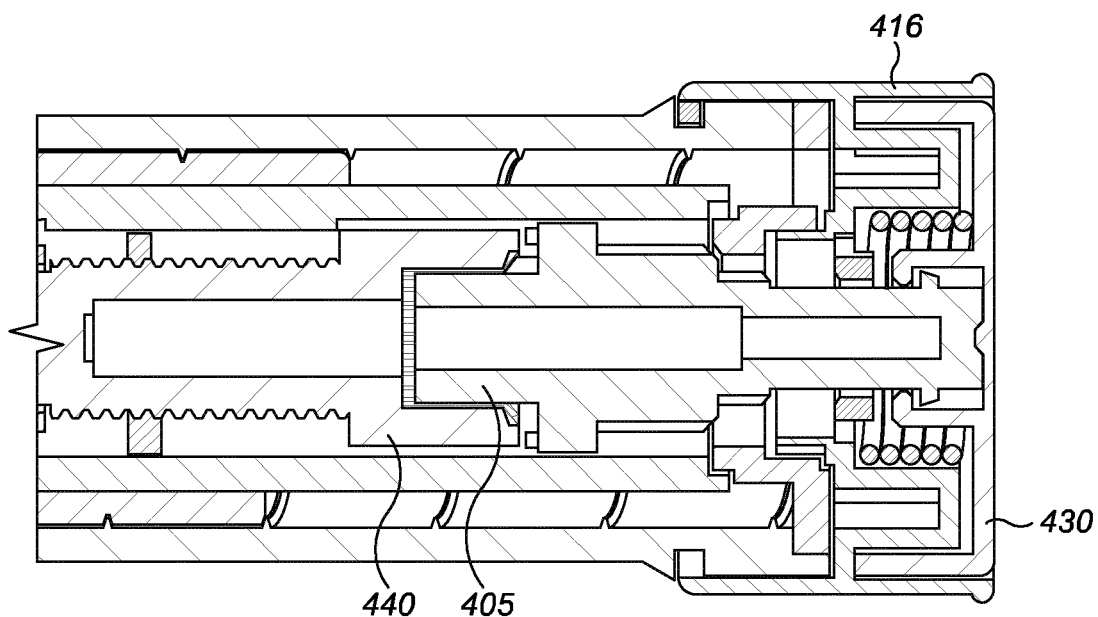
FIGS. 38A and 38B show the rear of the injection device after further pressing of the dose button, with the drive plate fully engaged with the drive shaft.
Figure 38B:
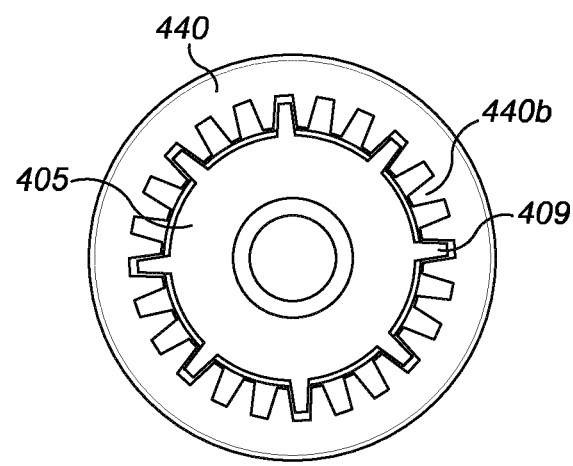

The engagement of the fourth set of drive plate splines 409 with the rear of the drive shaft 440 enables the drive shaft 440 to be driven by the spring 420 (FIG. 38B).

FIG. 38A shows the dose button 430 fully depressed, its axial travel limited by abutting the dose selector 416. The drive plate 405 and drive shaft 440 are fully engaged and able to rotate freely, driven by the drive spring 420 to deliver the desired dose of medicament.

During dose delivery, the one-way chassis ratchet 442 allows the drive shaft 440 to rotate with respect to the chassis 443, during which haptic feedback is provided to the user by the clicking of the chassis ratchet 442.

Figure 39:
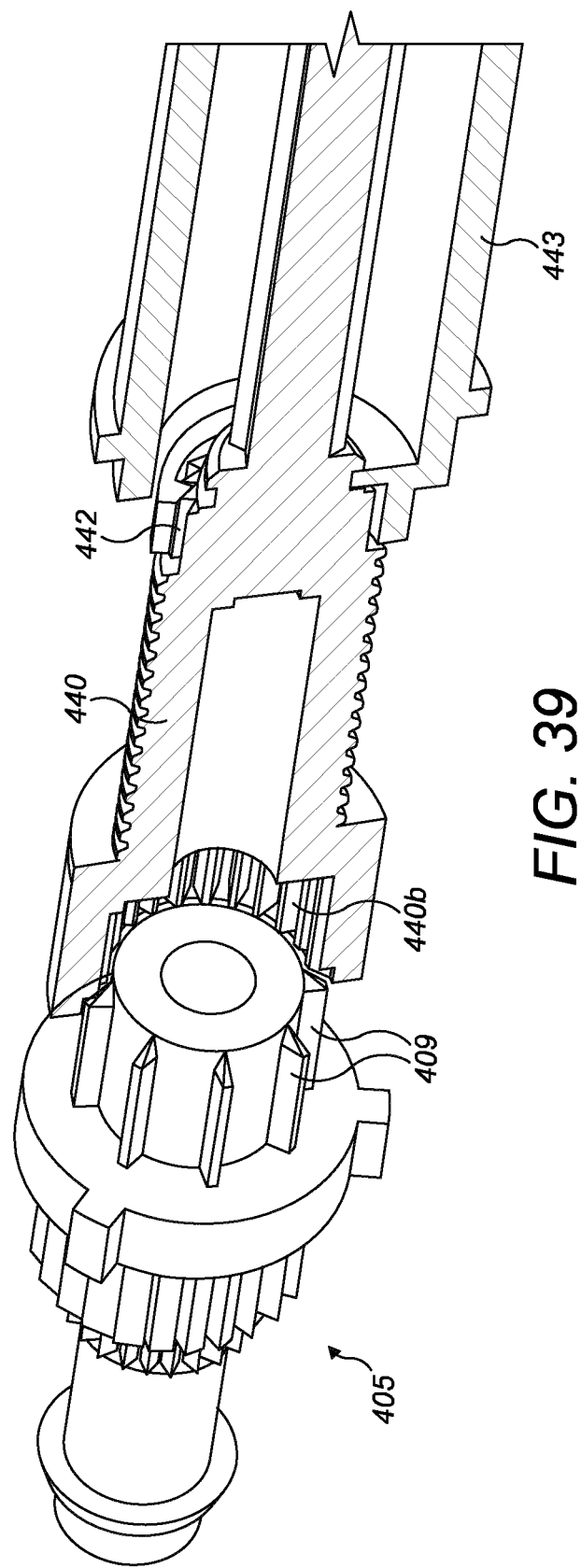
FIG. 39 is a perspective view, partly in cross-section, of the drive plate, drive shaft and chassis.

FIG. 39 shows how the fourth set of splines 409 on the drive plate 405 engage with the internal splines 440b of the drive shaft 440. The one-way chassis ratchet 442 is also visible at the rear of the chassis 443.

The relative rotational positions of the drive plate 405 and drive shaft 440 is important, to ensure the splines 409, 440b mesh smoothly (FIG. 38b). The splines 409, 440b are designed to allow up to 1 to 2 degrees of rotational displacement or play between splines 409, 440b. FIG. 40 shows typical relative positions of the hold ratchet pawl 410c and drive plate splines 406 (leftmost Figure), the chassis ratchet 442 and drive shaft 440 (centre Figure) and the drive plate splines 409 and internal drive shaft splines 440b (rightmost Figure). A 0.81° overlap does not prevent the drive plate 405 and drive shaft 440 from engaging smoothly.

FIG. 41 shows the most extreme possible relative positions of the hold ratchet pawl 410c and drive plate splines 406 (leftmost Figure), the chassis ratchet 442 and drive shaft 440 (centre Figure) and the drive plate splines 409 and internal drive shaft splines 440b (rightmost Figure). A 1.81° overlap still allows the drive plate 405 and drive shaft 440 to engage smoothly.

Figure 42:
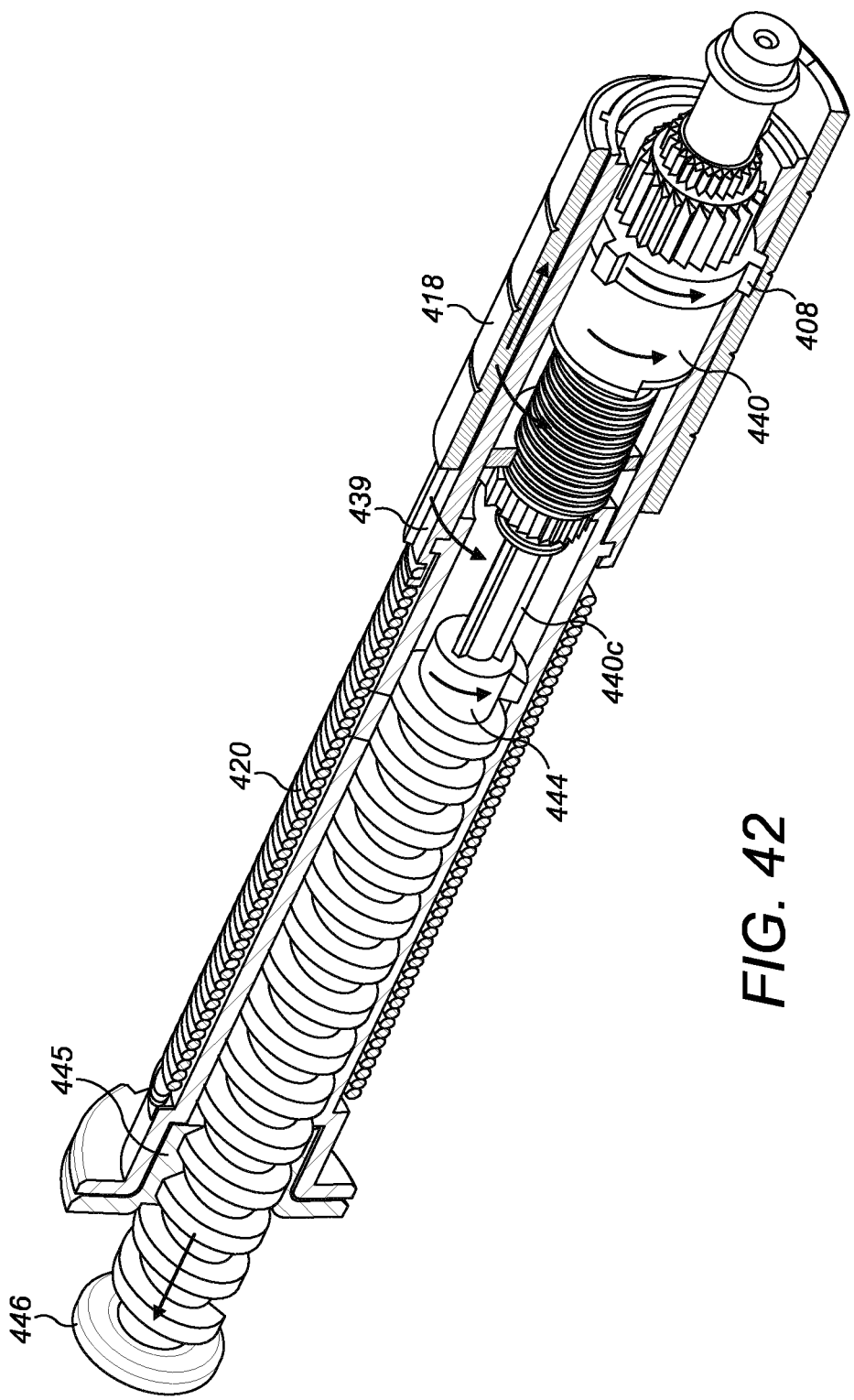
FIG. 42 is a perspective view, partly in cross-section, of injection device components involved in dose delivery.

Dose delivery can be summarised with reference to FIG. 42. The charged drive spring 420 is fixed at one end to the drive sleeve 439, turning it anti-clockwise. The drive sleeve 439 turns the number sleeve 418 which is splined thereto, causing the number sleeve 418 to move axially backwards because it is engaged with the screw thread 412b in the housing 412 (not shown).

The drive sleeve 439 turns the drive plate 405 because of splines 408. The drive plate 405 is engaged with the drive shaft 440 via splines 409 (not visible) and so the drive shaft 440 also turns.

The last dose nut 441 turns with the drive sleeve 439 and drive shaft 440 but does not move axially with respect thereto.

As the drive shaft 440 turns, it turns the hollow plunger 444 which is rotationally locked, or keyed, thereto. The thrust nut 445 causes the screw-threaded hollow plunger 444 to advance axially forwards, pushing the plunger bearing 446 against the cartridge stopper 426 (not shown) into the cartridge 424 (not shown) to expel the dose of medicament.

Figure 43:
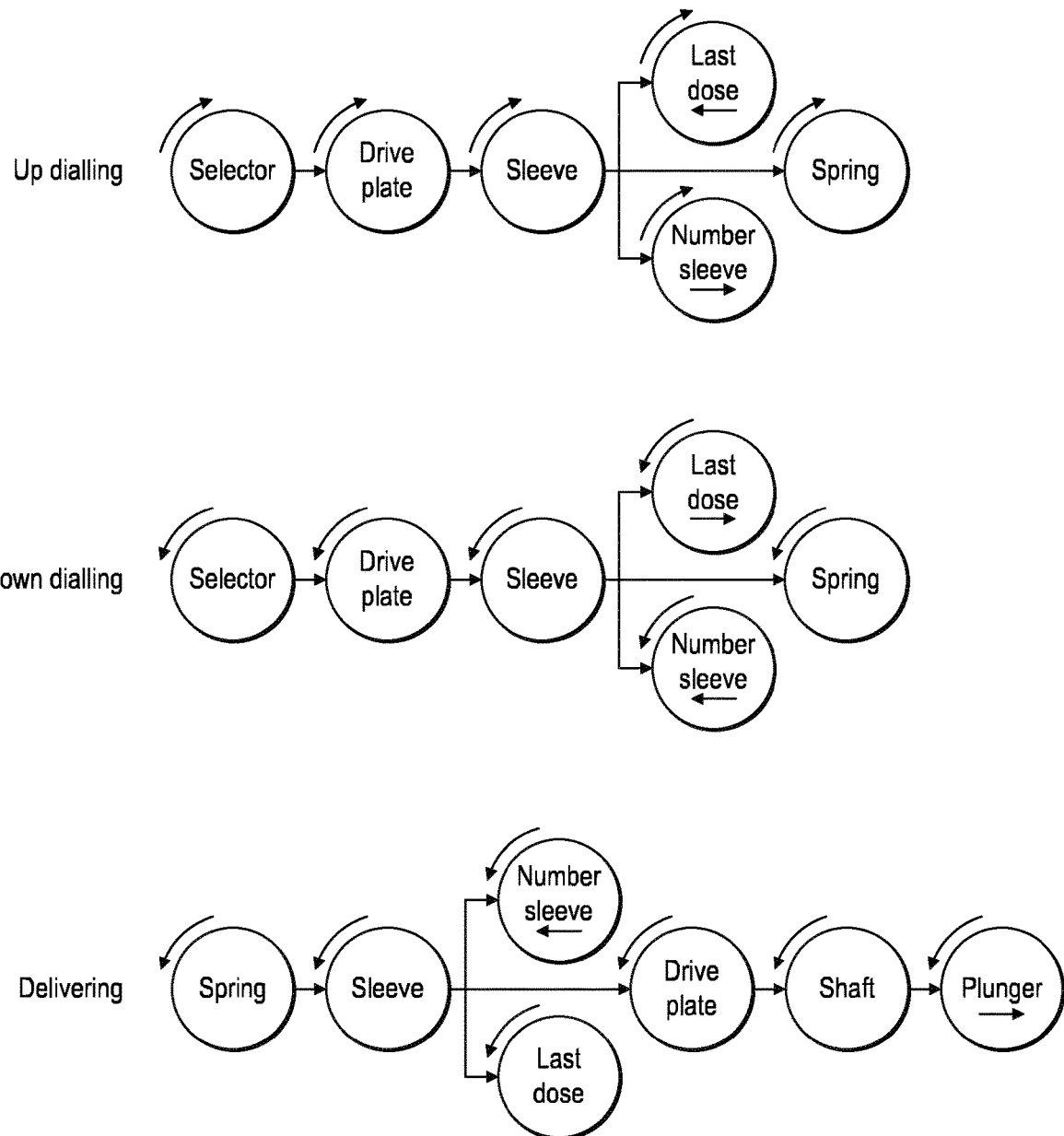
FIG. 43 summarises schematically the mechanical motion transfer of the injection device components.

FIG. 43 summarises schematically the mechanical motion transfer of the injection device components.

Figure 44:
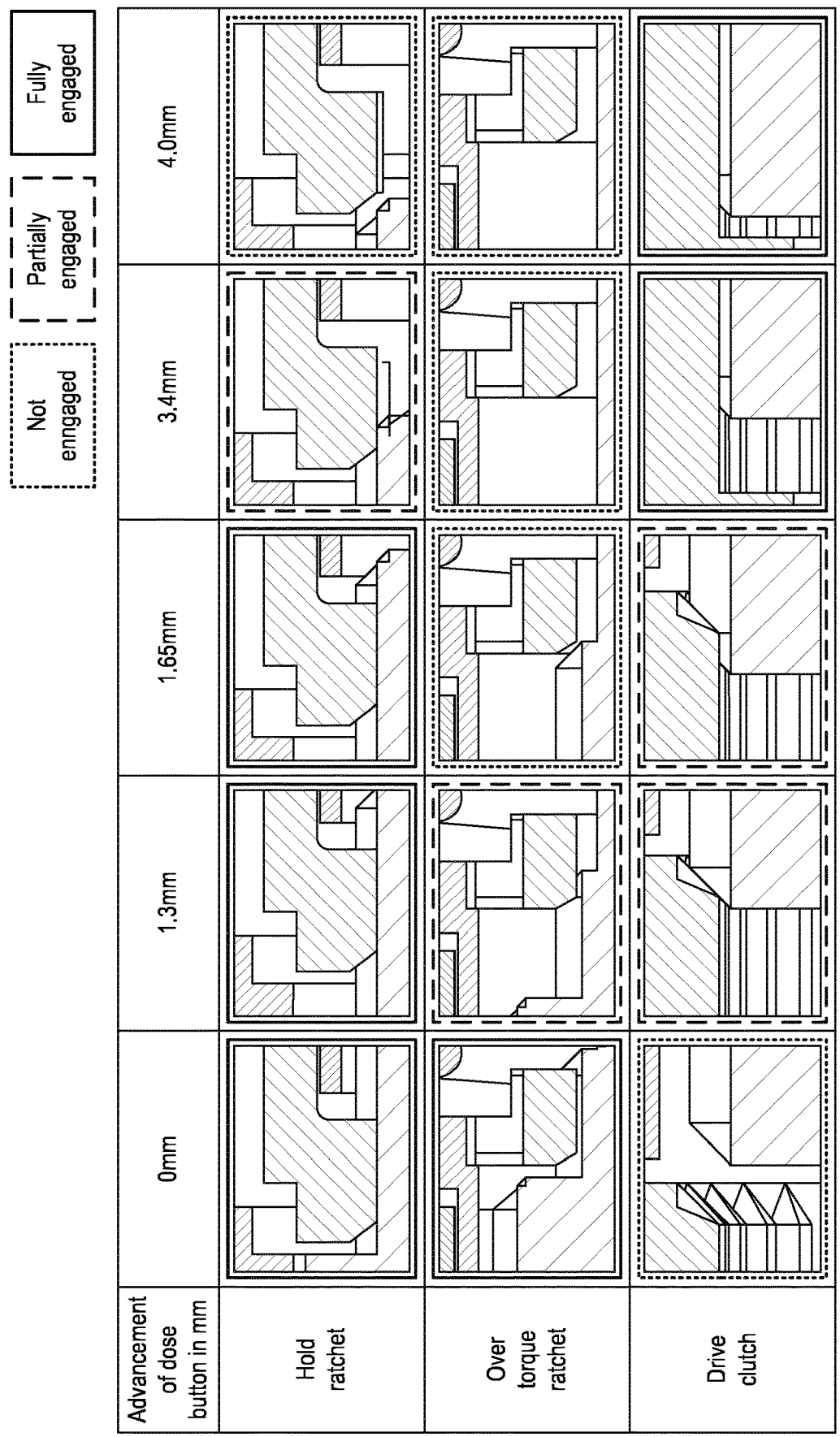
FIG. 44 is a diagrammatic summary of the key engagement points of the components of the injection device, at five stages of dose delivery.

FIG. 44 is a diagrammatic summary of the key engagement points of the components of the injection device, at five stages of dose delivery.

With reference to the above description, in the example embodiment it can be seen that the injection device 400 comprises:

a. a housing 412 having a longitudinal axis L;
b. an axially-depressible dose button 430;
c. a dose indicator 418;
d. a dose setting mechanism 405, 410, 416 operatively coupled to said dose indicator 418 and capable of setting a dose to be ejected from the injection device 400; and
e. a spring 420 capable of storing energy necessary for ejecting the dose from the injection device 400, wherein the spring is coupled to the dose setting mechanism such that a charging force can be transferred from the dose setting mechanism to the spring to increase the energy stored by the spring;

wherein the dose setting mechanism comprises an assembly of three components, including:
   a ratchet ring 410 rotationally and axially locked with respect to said housing 412, the ratchet ring including a ratchet component 410b, 410c, 410d;
   a drive plate 405 including a first set of splines 406 forming a ratchet arrangement with said ratchet component; and
   a dose selector 416 capable of being rotated about said longitudinal axis with respect to said housing to set the dose and including splines 416a for disengaging said ratchet arrangement,
   wherein said ratchet component 410b, 410c, 410d is capable of interacting with both the splines on the dose selector 416a and the splines on the drive plate 406.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

REFERENCE NUMERALS 400 injection device
L longitudinal axis
400a front end of the device
400b rear end of the device 405 drive plate
405a drive plate flange
406 first set of drive plate engagement splines/teeth (for hold ratchet)
407 second set of drive plate engagement splines/teeth (for over-torque ratchet)
408 third set of drive plate splines (for turning drive sleeve)
409 fourth set of drive plate splines (for engaging drive shaft)
410 ratchet ring
410a ratchet ring notches for engaging with housing
410b ratchet ring ratchet arm (for hold ratchet)
410c ratchet ring first pawl
410d ratchet ring second pawl
410e ratchet ring hard stop (for number sleeve)
412 housing
412a aperture in the housing
412b housing thread
412c rotary endstop for number sleeve on internal surface of housing
416 dose selector
416a dose selector disengagement splines/teeth (for hold ratchet)
416b dose selector ratchet pawl (for over-torque ratchet)
416c dose selector grip formations
418 number sleeve
418a number sleeve longitudinal grooves
418b number sleeve helical groove
420 drive spring
424 medicament cartridge
425 cartridge holder
426 cartridge stopper
430 dose button
431 dose button spring
439 drive sleeve
439a external drive sleeve splines
439b internal drive sleeve splines
440 drive shaft
440a drive shaft rotary endstop for last dose nut
440b drive shaft internal splines (for engaging drive plate)
440c drive shaft external splines (for keying to hollow plunger)
441 last dose nut
441a last dose nut external grooves
441b last dose nut endstop
442 chassis ratchet arrangement
443 chassis
444 hollow plunger
445 thrust nut
446 plunger bearing

The invention claimed is:

1. An injection device comprising:
   a. a housing having a longitudinal axis;
   b. an axially-depressible dose button;
   c. a dose indicator;
   d. a dose setting mechanism operatively coupled to said dose indicator and capable of setting a dose to be ejected from the injection device; and
   e. a spring capable of storing energy necessary for ejecting the dose from the injection device, wherein the spring is coupled to the dose setting mechanism such that a charging force can be transferred from the dose setting mechanism to the spring to increase the energy stored by the spring;
   wherein the dose setting mechanism comprises an assembly of three components, including:
   a ratchet ring rotationally and axially locked with respect to said housing, the ratchet ring including a ratchet component;
   a drive plate including a first set of splines forming a ratchet arrangement with said ratchet component; and
   a dose selector capable of being rotated about said longitudinal axis with respect to said housing to set the dose and including splines,
   wherein said ratchet component is capable of interacting with both the splines on the dose selector and the first set of splines on the drive plate,
   wherein said ratchet component is configured to be pushed radially outwards by said splines on the dose selector and comprises a first pawl capable of interacting with the splines on the dose selector and for disengaging said ratchet arrangement a second pawl capable of interacting with the first set of splines on the drive plate.

2. The injection device of claim 1 wherein the dose selector is operatively connectable to the dose indicator via said ratchet arrangement, the ratchet arrangement preventing counter-rotation of the dose indicator during dose setting.

3. The injection device of claim 2 wherein the ratchet arrangement is disengageable from the dose selector by axial depression of the dose button.

4. The injection device of claim 1 further comprising an over-torque feature located between the dose selector and the spring, the over-torque feature being actuatable, when the rotation of the dose selector causes the charging force to exceed a defined limit, to reduce the charging force transferred from the dose selector to the spring.

5. The injection device of claim 4 wherein the over-torque feature is capable of reducing the charging force transferred from the dose selector to the spring to substantially zero.

6. The injection device of claim 4 wherein the over-torque feature comprises a ratchet arrangement between said drive plate and said dose selector.

7. The injection device of claim 4 wherein the ratchet arrangement comprises a ratchet pawl on said dose selector and a second set of splines on said drive plate.

8. The injection device of claim 1 wherein the spring is a torsion spring and the charging force transferred to the spring is a charging torque.

9. The injection device of claim 1 further comprising a drive assembly having a rotational to axial coupling, where the drive assembly is rotationally drivable by the spring and is arranged to provide an axial force for ejecting the dose from the injection device.

10. The injection device of claim 1 wherein the spring is fixed at one end to said housing and fixed at the other end to a rotatable drive sleeve.

11. The injection device of claim 10 wherein the drive plate further comprises a second set of splines for engaging and turning said drive sleeve.

12. The injection device of claim 11 wherein the drive plate further comprises a third set of splines for engaging a drive assembly.

13. The injection device of claim 1 wherein the dose indicator comprises a number sleeve.

14. The injection device of claim 13 wherein said ratchet ring includes a rotary endstop for said number sleeve.

15. The injection device of claim 1 wherein said first and second pawl are provided on a single ratchet arm.

16. The injection device of claim 15 wherein said ratchet arm is radially-moveable.

17. The injection device of claim 1 further comprising a medicament container.

18. The injection device of claim 17 wherein the medicament container comprises a pre-filled syringe or cartridge.

19. The injection device of claim 17 further comprising a medicament contained in the medicament container.

20. The injection device of claim 19 wherein the medicament is selected from the group comprising: antipsychotic substances including risperidone, hormones, antitoxins, substances for the control of pain, immunosuppressives, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity.

* * * * *